(12) United States Patent
Kim et al.

(10) Patent No.: US 7,939,290 B2
(45) Date of Patent: May 10, 2011

(54) METHOD FOR ANALYZING THE ACTIVITY OF LIPOXYGENASE USING A WATER-SOLUBLE SUBSTRATE

(75) Inventors: Mee-Ree Kim, Daejeon (KR); Dai-Eun Sok, Daejeon (KR); Long-Shuang Huang, Daejeon (KR)

(73) Assignee: Chungnam National University Industry Collaboration Foundation, Daejeon (KR)

( * ) Notice: Subject to any disclaimer, the term of this patent is extended or adjusted under 35 U.S.C. 154(b) by 825 days.

(21) Appl. No.: 11/801,482

(22) Filed: May 9, 2007

(65) Prior Publication Data

US 2007/0264679 A1    Nov. 15, 2007

(51) Int. Cl.
*C12Q 1/26* (2006.01)
(52) U.S. Cl. .............................. 435/25; 435/4
(58) Field of Classification Search .................. None
See application file for complete search history.

(56) References Cited

U.S. PATENT DOCUMENTS

2007/0122862 A1*   5/2007   Borch et al. ................... 435/18

FOREIGN PATENT DOCUMENTS

WO    WO 2005040410 A1 *  5/2005

OTHER PUBLICATIONS

Brash A.R. et al. Analysis of a Specific Oxygenation Reaction of Soybean Lipoxygenase- 1 with Fatty Acids Esterified in Phospholipids, Biochemistry, 1987, vol. 26, pp. 5465-5471.*
Jimémez M. et al. A continuous spectrophotometric assay for phospholipase A2 activity, Analytical Biochemistry, (2003), vol. 319, pp. 131-137.*
Marinho H.S. et al. Role of Glutathione Peroxidase and Phospholipid Hydroperoxide Glutathione Peroxidase in the Reduction of Lysophospholipid Hydroperoxides, Free Radical Biology & Medicine, 1997, vol. 22, No. 5, pp. 871-883.*
Huang L.S.. et al. Linoleoyl lysophosphatidylcholine is an efficient substrate for soybean lipoxygenase-1, Archives of Biochemistry and Biophysics, 2006 (Available online Oct. 6, 2006), vol. 455, pp. 119-126.*
Huang, Long Shuang et al., "Oxygenation of Arachidonoyl Lysophospholipids by Lipoxygenases from Soybean, Porcine Leukocyte, or Rabbit Reticulocyte," Journal of Agricultural and Food Chemistry, 2008, 56, pp. 1224-1232.
Huang, Long Shuang et al., "Oxygenation of 1-Docosahexaenoyl Lysophosphatidylcholine by Lipoxygenases: Conjugated Hydroperoxydiene and Dihydroxytriene Derivatives," Lipids (2007), 42, pp. 981-990.
Huang, Long Shuang et al., "Linoleoyl lysophosphatidic acid and linolyeoyl lysophosphatidylcholine are efficient substrates for mammalian lipoxygenases," ScienceDirect, Biochemica et Biophysica Acta 1170 (2007), pp. 1062-1070.
Sok, Dai-Eun et al., "Conversion of a-Linolenic Acid to Dihydro(pero)xyoctadecatrienoic Acid Isomers by Soybean and Potato Lipoxygenases," Journal of Agricultural and Food Chemistry, (1994), 42, pp. 2703-2708.
Kim, Mee Ree et al., "Inactivation of Potato Lipoxygenase by Hydroperoxy Acids As Suicide Substrates," Biochemical and Biophysical Research Communications, vol. 164, No. 3, Nov. 15, 1989. (Abstract).
Sok, Dai-Eun et al., "The Possible Role of 9(S)-Hydroperoxyoctadecatrienoic Acid As a Suicide Substrate of Soybean Lipoxygenase," Biochemical and Biophysical Research Communications, vol. 162, No. 3, Aug. 15, 1989. (Abstract).

* cited by examiner

*Primary Examiner* — Jon P Weber
*Assistant Examiner* — Satyendra K Singh
(74) *Attorney, Agent, or Firm* — Edwards Angell Palmer & Dodge LLP; Kingsik Kim

(57) ABSTRACT

The present invention discloses methods for analyzing the activity of lipoxygenase by using polyunsaturated lysophosphatidylcholine as a water-soluble substrate. In these methods, lipoxygenase activity can be analyzed without using detergents in reaction solution.

9 Claims, 18 Drawing Sheets

R: linoleoyl, arachidonoyl, docosahexaenoyl

A

B

METHOD FOR ANALYZING THE ACTIVITY OF LIPOXYGENASE USING A WATER-SOLUBLE SUBSTRATE

CROSS-REFERENCE TO RELATED APPLICATION

The present application claims, under 35 U.S.C. §119, the benefit of Korean Patent Application No. 10-2006-0041501, filed May 9, 2006, the entire contents of which are hereby incorporated by reference.

BACKGROUND OF THE INVENTION

1. Technical Field

The present invention relates to a simple and correct method for analyzing lipoxygenase activity. More specifically, it relates to a simple method for analyzing lipoxygenase activity by measuring the absorbance of material produced by oxidation of polyunsaturated lysophosphatidylcholine by lipoxygenase.

2. Background Art

Lipoxygenase (linoleate: oxygen oxidoreductase, EC 1.13.11.12; hereinafter called as "LOX"), a nonheme iron-containing enzyme, catalyzes the addition of molecular oxygen to fatty acids containing at least one (Z,Z)-pentadiene system to give corresponding hydroperoxides (W. L. Smith, W. E. Lands, J. Biol. Chem. 247 (1972) 1038-1047; S. Yamamoto, Biochem. Biophys. Acta 1128 (1992) 117-131). Lipoxygenation occurs when 1,4-(Z,Z)-pentadiene is oxidized by LOX.

The nomenclature of lipoxygenases is based on the specificity of the enzymes with respect to their substrates. For example, 12-LOX oxygenates arachidonic acid at carbon-12. The stereochemistry of the reaction can be specified when necessary (e.g. 12R-LOX or 12S-LOX). Where more than one enzyme have the same specificity, they may be named after the tissue in which they are found. For example, there can be platelet, leukocyte and epidermal types of 12-LOX.

Four main enzyme types with positional specificities occur in animal tissues, i.e. 5-LOX, 8-LOX, 12-LOX, and 15-LOX. The first step in the reaction involving 5-LOX is the abstraction of a hydrogen atom from carbon-7 by ferric hydroxide, which involves a proton-coupled electron transfer by which the electron is transferred directly to the iron (III) to produce a substrate radical. The structure of this radical is uncertain, as are the details of the next steps in which an oxygen atom is added, and the cis-double bond in position 5 migrates to position 6 with a change to the trans-configuration leaving the hydroperoxyl moiety in position 5. The resulting product is 5S-hydroperoxy-6t,8c,11c,14c-eicosatetraenoic acid (5-HPETE). 8-, 12- and 15-LOX operate in the same way to give analogous products. 15-LOX has a broader specificity and is able to oxidize linoleate to 13-hydroperoxyoctadecadienoate (and in part to the 9-isomer). It is also able to utilize arachidonate bound to phospholipids as a substrate hence the interest in the role of the enzyme in membrane disruption and in disease states is increased.

Lipoxygenase uses unsaturated fatty acids liberated from biomembranes by phospholipase A2 (Cirino, *Biochem. Pharmacol.* 55 (1998), p. 105; Farooqui et al, *J. Neurochem.* 69 (1997), pp. 889-901; Dennis, *J. Biol. Chem.* 269 (1994), p 13057). Although some of LOXs directly can oxidize certain phospholipids or triglycerides, free polyunsaturated fatty acids are preferable substrate (W. L. Smith, W. E. Lands, J. Biol. Chem. 247 (1972) 1038-1047; S. Yamamoto, Biochem. Biophys. Acta 1128 (1992) 117-131).

In certain tissues, particularly mammalian heart tissues, lipoxygenase oxidizes biomembranes or phospholipids (Heinrikson et al, J. Biol. Chem. 252 (197), P. 4913; Schalkwijk et al., Biochem. Biophys. Res. Commun. 174 (1991), p. 268; Petit et al., J. Neurochem. 64 (1995), p. 139) and the growth of reticulocytes are associated with lipoxygenase, suggesting that lipoxygenase may intervene biological reaction by influencing the variation of cell membrane structure (Brash et al., Biochemistry, 1987, 26; 5465-5471; Murray et al., Arch Biochem Biophs. 1988; 265; 514-523). A recent study reported that lipoxygenase is related with the oxidation of low density lipoprotein (LDL) and that soybean lipoxygenase as well as 15-lipoxygenase also oxidize low density lipoproteins (Funk et al, Trends Cardiovasc. Med. 2001; 11, 116). Another recent study reported that in the presence of deoxycholate, lipoxygenase can convert arachidonyl and linoleoyl group in phospholipids exclusively to 15 (S)-hydroperoxyeicosatetraenoic acid and 13 (S)-hydroperoxyoctadecadienoate analogs, respectively (Perez-Gilabert et al. Arch Biochem. Biophy. 1998; 354, 18). In this regard, fatty acids bound to phospholipids with ester bond may be selectively oxidized by lipoxygenase. That is, it is expected that the end part of acyl group of fatty acid derivatives bound to phospholipids can be oxidized more easily.

Lipoxygenases are ubiquitously distributed in animals and plants and have various biological functions such as inflammation mediation, signal transduction mediation etc. [G. Cirino, *Biochem. Pharmacol.* 55 (1998), p. 105; Farooqui et al., *J. Neurochem.* 69 (1997), p. 889). In mammalian systems, the direct effect of lipoxygenases on phospholipids and biomembranes (Kühn et al, J. Biol. Chem. 265 (1990) 18351-18361; Brash et al, Biochemistry 26 (1987) 5465-5471; Jung et al, Biochem. Biophys. Res. Commun. 130 (1985) 559-566; Takahashi et al, Eur. J. Biochem. 218 (1993) 165-171) suggests a role of lipoxygenases in some processes such as cellular maturation, which implies a change in the structure of the membrane (Rapoport et al, Biochim. Biophys. Acta 864 (1986) 471-495; Conrad et al, Proc. Natl. Acad. Sci. USA 89 (1992) 217-221). Additionally, soybean lipoxygenase-1 (LOX-1) is known to induce oxidation of phospholipids in low-density lipoprotein (LDL) directly with major implications for the onset of atherosclerosis, where phospholipids exist as a solubilized form (Funk et al, Trends. Cardiovasc. Med. 11 (2001) 116-124).

Lipoxygenation is highly dependent upon substrate availability. That is, prior art lipoxygenase substrates such as unsaturated fatty acids or polyunsaturated phosphatidylcholines have been used as their salt forms, e.g., sodium or ammonium form due to their fat-solubility and insolubility in a buffer solution. For measuring lipoxygenase activity, lipoxygenase substrates, linolate and arachidonic acid have to be converted to their salt forms such as Na-linolate or Na-arachidonate respectively and dispersed by a detergent added to the reaction solution. Detergents used for this purpose are Tween 20 and deoxycholate (G. Began et al. Biochemistry (1999) 38; 13920). In the presence of deoxycholate, polyunsaturated acyl moieties in phosphatidylcholine were converted by lipoxygenase to the respective hydroperoxides, although the oxidation rate was much lower for phosphatidylcholine substrate than free fatty acid substrate. For example, arachidonyl and linoleoyl moieties in phosphatidylcholine were converted to exclusively to 15 (S)-hydroperxyeicosatetraenoic acid and 13 (S)-hydroperoxyoctadecadienoate analogs, respectively, suggesting that fatty acids esterified in phospholipids can be subjected to highly specific oxygenation by lipoxygenase (Brash et al, Biochemistry 26 (1987) 5465-5471; Arai et al, Lipids 30 (1995) 135-140).

Lipoxygenation of dilinoleoyl phosphatidylcholine having 2 ester bonds has to be faster than that of linoleic acid. However, it is about 4 times slower (M. Perez-Gilabert et al., Arch. Biochem. Biophys. 1998; 354, 18) since although dilinoleoyl phosphatidylcholine can be used as a LOX substrate, the reaction speed is limited for that structure being itself bilayer.

The above-described prior art methods for measuring lipoxygenase activity have problems in that a detergent is required to be used with concentration higher than micellation concentration and that solubilization process can take a long time. In addition, when there exists LOX in tissues or cells, unsatisfied results can occur.

There is thus a need for a new method for analyzing lipoxygenase activity.

The information disclosed in this Background section is only for enhancement of understanding of the background of the invention and should not be taken as an acknowledgement or any form of suggestion that this information forms the prior art that is already known to a person skilled in the art.

SUMMARY OF THE INVENTION

The present invention has been made to provide a simple and correct method for analysis of lipoxygenase that can solve the above-described problems associated with prior art methods.

In one aspect, the present invention provides a method for analyzing the activity of lipoxygenase, comprising the steps of: (a) adding polyunsaturated lysophosphatidylcholine as water-soluble substrate into a reaction solution; (b) adding lipoxygenase into the reaction solution; and (c) measuring spectral characteristics of the reaction solution to obtain spectral data.

Preferably, the polyunsaturated lysophosphatidylcholine is a water-soluble substrate selected from the group consisting of 1-linoleoyl lysophosphatidylcholine, 1-arachidonoyl lysophosphatidylcholine and docosahexaenoyl lysophosphatidylcholine.

The lipoxygenase can originate from a plant or an animal. Preferably, it can originate from a plant cell or an animal cell.

In a preferred embodiment, the polyunsaturated lysophosphatidylcholine may comprise one or more radioisotope of $^{14}C$ or $^{32}P$.

Preferably, the lipoxygenase activity may be measured by using absorbance at 234 nm.

Also preferably, it may be measured by measuring peroxide of the water-soluble substrate. Preferred examples of the peroxide include 1-(13-hydroperoxy)linoleoyl lysophosphatidylcholine, 1-(15-hydroperoxy) arachidonoyl lysophosphatidylcholine, and 1-(17-hydroperoxy)docosahexaenoyl lysophosphatidylcholine.

In a preferred method, the measurement of lipoxygenase activity may be conducted in the reaction solution having the range of pH 5-11.

In another preferred method, the concentration of the substrate may be in the range of 0.0001-1 mM in the reaction solution.

BRIEF DESCRIPTION OF THE DRAWINGS

These, and other features and advantages of the invention, will become clear to those skilled in the art from the following detailed description of the preferred embodiments of the invention rendered in conjunction with the appended drawings in which like reference numerals refer to like elements throughout.

DETAILED DESCRIPTION OF THE PREFERRED EMBODIMENTS

Figure 1:
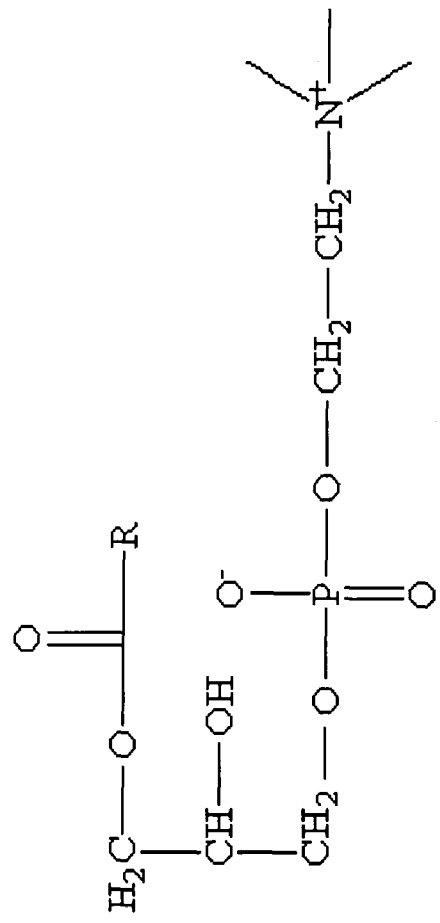
FIG. 1 is a schematic diagram showing the chemical structure of polyunsaturated fatty acyl lysophosphatidylcholine.

Other objects and advantages of the present invention will become apparent upon reference to the following detailed description of the invention. And, while the invention is described in connection with certain preferred embodiments and procedures, it is to be understood that the invention is not to be limited to those embodiments and procedures. On the contrary, all alternatives, modifications, and equivalents as can be included within the scope and spirit of the invention defined in the appended claims are intended to be covered.

As used herein, the terms "lipoxygenase" and "LOX" are used interchangeably. These terms refer to any member of a group of enzymes that can catalyze the hydroperoxidation of polyunsaturated fatty acids in the first step of fatty acid metabolite synthesis. In higher plants, linoleic acid and linolenic acid are oxygenated by the action of lipoxygenase (LOX) to produce hydroperoxide fatty acids. The lipoxygenase can originates from plants or animals.

As used herein, the term "polyunsaturated lysophosphatidylcholines" means a lysophosphatidylcholines bound with a fatty acid containing at least one (Z,Z)-pentadiene structure. Preferably, polyunsaturated lysophosphatidylcholine can be selected from the group consisting 1-linoleoyl lysophosphatidylcholine, 1-arachidonoyl lysophosphatidylcholine and docosahexaenoyl lysophosphatidylcholine. These polyunsaturated lysoPCs may contain one or more radioisotope of $^{14}C$ or $^{32}P$ for detection in mass spectroscopy or HPLC.

As used herein, the terms "lysophosphatidyl cholines," "LysoPC" and "LPC" are used interchangeably. They refer to 1-Acyl-2-Hydroxy-sn-Glycero-3-Phosphocholine.

As used herein, the term enzyme "activity" refers to the ability of an enzyme to convert a substrate to a product. For example, lipoxygenases convert a fatty acid to hydroperoxide fatty acids.

As used herein, the term "measuring with spectrophotometer" refers to measurements of changes in the absorption of light. Turbidity measurements, measurements of visible light absorption, and measurement of ultraviolet light absorption are examples of spectral measurements. Preferable absorption wavelength of light is 234 nm.

Hereinafter, the present invention will be described in further detail with reference to examples. It is to be understood, however, that these examples are for illustrative purposes only and are not to be construed to limit the scope of the present invention.

EXAMPLE 1

Preparation of 1-linoleoyl Lysophosphatidylcholine, 1-arachidonyl Lysophosphatidylcholine and 1-docosahexenoyl Lysophosphatidylcholine 1-linoleoyl-lysophosphatidylcholine, 1-arachidonyl lysophosphatidylcholine and 1-docosahexenoyl lysophosphatidylcholine were prepared from $PLA_2$-catalyzed hydrolysis of dilinoleoyl phosphatidylcholine, diarachidonyl phosphatidylcholine and didocosahexenenoly phosphatidylcholine respectively, by known methods with some modification (M. Jimenez-Ateinzaer et al., Lipids. 2003; 38, 677; M. Jimenez et al., Anal Biochem. 2003; 319, 131). More particularly, dilinoleoyl phosphatidylcholine (Avanti Polar Lipid Inc, Alasbaster, Ala., USA) (2 mg), dissolved in chloroform, was dispersed in a glass bottle and then suspended in 2.5 ml of Tris buffer (pH 8.0, Sigma, Saint Louis, Mo., USA). The hydrolysis was started by adding $PLA_2$ (15 units/mL, Sigma, Saint Louis, Mo., USA), and allowed to react with constant stirring for 1 hr at 25° C. After the reaction for 1 hr, 1-linoleoyl lysophosphatidylcholine was purified by silica gel TLC (25 TLC plates, 20×20 cm silica gel 60 F254; Merck, Darmstadt, Germany) in the solvent system (chloroform:methanol:ammonia:water=65:30:8:2). The spot, containing 1-linoleoyl lysophosphatidylcholine, was scratched off, extracted with methanol (10 ml). And after sonication (30 min, on ice) at 25° C., the extract was centrifuged at 8000 rpm for 5 min. The supernatant was removed by vacuum filtration from the silica gel and concentrated in methanol. 1-arachidonyl lysophosphatidylcholine and 1-docosahexanoyl lysophosphatidylcholine were prepared in the same manner of 1-linoleoyl lysophosphatidylcholine except that the starting material was diarachidonyl phosphatidylcholine and didocosahexaenenoyl phosphatidylcholine respectively.

EXAMPLE 2

Analysis of Lipoxygenase Activity with a 1-linoleoyl Lysophosphate

Materials & Methods

Dilinoleoyl phosphatidylcholine (DLPC, 99%), soybean lysophosphatidylcholine and 1-plamitoyl-lysophosphatidylcholine were obtained from Avanti Polar Lipid (Alabaster, Ala., USA). Soybean lipoxygenase (lipoxidase Type I-B, EC 1.13.11.12, 187,400 Sigma units/mg protein), cholesterol esterase (EC3.1.1.13, bovine pancreas), phospholipase $A_2$ (E.C. 3.1.1.4, honey bee venom), 13(S)-hydroxyoctadecadienoic acid (HODE), 9(S)-HODE, and Tween 20 were purchased from Sigma-Aldrich Corp (St. Louis, Mo., USA). HPLC solvents were all of HPLC grade, and other chemicals were of analytical grade.

Assay of Lipoxygenase 1 Activity in Oxygenation of Linoleate

Lipoxygenase-1 (LOX-1) activity was monitored at 25° C. by measuring the increase in absorbance at 234 nm due to the formation of hydroperoxide ($\epsilon_{234}$=25,000 $M^{-1}$ $cm^{-1}$) as previously reported (Axelrod et al, Methods Enzymol. 71 (1981) 441-451; Egmond et al, Eur. J. Biochem. 61 (1976) 93-100). The reaction was started by including LOX-1 (0.0065 units/ml) in 50 mM borax buffer, pH 9.0 (0.5 ml) containing sodium linoleate (100 μM), which was prepared by suspending sodium linoleate (7 mg) in 2.5 ml of distilled water containing Tween 20 (7 mg). One unit is defined as the amount of LOX-1 that can produce one micromole of conjugated diene per min.

Purification of Soybean Lipoxygenase-1

LOX-1 was purified from soy bean lipoxidase preparation (Type I-B) according to the method of Finazzi Agro et al (Finazzi-Agro et al, Biochim. Biophys. Acta 326 (1973) 462-470). Briefly, soybean LOX-1 (100 mg) was dissolved in 0.1 M phosphate buffer (pH 6.8), and applied to DEAE Sephacel (1.5×25 cm). The bound enzyme was eluted by concentration gradient (0.1-0.25 M) of phosphate buffer (pH 6.8), and the fractions of LOX-1 activity, showing a relatively homogeneous band in SDS-PAGE, were used as LOX-1 (Specific activity, 114.3 units/mg protein). Protein amount was determined according to Lowry method (O. H. Lowry, N. J. Rosenbrough, A. L. Farr, R. J. Randall, J. Biol. Chem. 193 (1951) 265-275).

Preparation of 1-linoleoyl Lysophosphatidylcholine (Linoleoyl-lysoPC) from Dilinoleoyl Phosphatidylcholine (DLPC)

Linoleoyl-lysoPC was prepared from $PLA_2$-catalyzed hydrolysis of DLPC as described previously with some modification (Pérez-Gilabert et al, Arch. Biochem. Biophys. 354 (1998) 18-23). More particularly, DLPC (2 mg), dissolved in chloroform, was dried under $N_2$, and then rapidly dispersed in 10 ml of 50 mM borax buffer, pH 8.5 containing 100 mM $CaCl_2$. The hydrolysis was started by adding $PLA_2$ (~120 units), and allowed to continue under $N_2$ with constant stirring for 1 hr at 25° C. The reaction mixture was loaded directly onto $C_{18}$ Sep-pack column (3×1 cm), which was washed with three volumes of distilled water, and finally lysophospholipid products was eluted with methanol. Next, linoeoyl-lysoPC was purified by silica gel TLC in the solvent system (chloroform:methanol:concentrated ammonia water: $H_2O=90:54:5.5:5.5$) as described previously (Azzi et al, Membrane proteins, Springer-Verlag Berlin Heidelberg Inc., New York, 1981, pp. 43-49). The spot, containing linoleoyl-lysoPC, was scratched off, extracted with methanol (10 ml) three times, and dried under $N_2$.

pH-Dependent Oxygenation of Linoleic Acid or 1-linoleoyl lysopc by LOX-1

LOX-1 (0.02 units/ml) was incubated with linoleoyl-lysoPC (100 μM) in 500 μl of buffers of various pHs (pH 6.0-11) at 25° C. as described before (Began et al, Biochemistry 38 (1999) 13920-13927); 200 mM phosphate (pH 6-8), 50 mM borax (pH 8.5-9.5), 300 mM sodium bicarbonate (pH 10-11). Separately, the oxygenation was started by including LOX-1 (0.02 units/ml) in the reaction mixture containing sodium linoleate (100 μM) in the presence of Tween 20 (25 μM).

Effect of Substrate Concentration on LOX-1-catalyzed Oxygenation of Linoleic Acid or Linoleoyl-LysoPC Soybean LOX-1 (0.02 units/ml) was incubated with linoleic acid or linoleoyl-lysoPC of various concentrations in 500 μl of 50 mM borax buffer, pH 9.0 at 25° C.

RP-HPLC Separation of Oxygenation Products of Linoleoyl-LysoPC

Oxygenation of linoleoyl-lysoPC was started by including soybean LOX-1 (0.5 units/ml) in 150 μl of 50 mM borax buffer, pH 9.0 containing linoleoyl-lysoPC (1 mM). After 10 min, the reaction products were subjected to RP-HPLC (Hitachi L-7100 pump, Japan) equipped with $C_{18}$ column (300×7.8 mm, Phenomenex, USA), which was eluted at a flow rate of 1 ml/min with gradient solvent system of 0.1% formic acid/acetonitrile (solvent B) in 0.1% formic acid/$H_2O$ (solvent A); 25% from 0 to 10 min; 25-45% from 10 to 25 min; 45% from 25 to 55 min; 45-100% from 55 to 70 min.

LC/ESI-MS Analysis

LC-MS was performed using a MSDI spectrometer (HP 1100 series LC/MSD, Hewlett Packard, USA) equipped with ZORBAX Eclipse XDB $C_{18}$ column (5 μm, 50×4.6 mm, Agilent Technologies, USA), which was eluted (1 ml/min) with gradient solvent of 0.1% formic acid/acetonitrile (solvent B) in 0.1% formic acid/$H_2O$ (solvent A): 0-45% from 0 to 10 min and 45% from 10 min to 55 min. The products from oxygenation of linoleoyl-lysoPC were monitored by ESI-MS system using positive-ion modes.

Identification of Peroxy Linoleic Acid Generated from Cholesterol Esterase-Catalyzed Hydrolysis of Peroxy Linoleoyl-LysoPC Linoleoyl-lysoPC or soybean lysoPC (1 mM) was incubated with LOX-1 (0.5 units/ml) under stirring in 10 ml of 50 mM borax buffer (pH 9.0). After 30 min incubation, cholesterol esterase (5 units/ml) was included into the above mixture to hydrolyze 1-acylated lysophosphatidylcholine (DiPersio et al, J. Biol. Chem. 265 (1990) 16801-16806). Separately, linoleoyl-lysoPC or soybean lysoPC was incubated with LOX-1 in 50 mM phosphate buffer (pH 7.4) for 30 min. Then, the above mixture was acidified to inactivate remaining LOX-1 activity, followed by the pH adjustment to pH 9.0 with borate buffer for the cholesterol esterase hydrolysis. After another 60 min incubation, the oxygenation products were loaded into $C_{18}$ Sep-pack column (3×1 cm), which was washed with distilled water. The methanol eluate was concentrated, and then an aliquot (100 μ) was subjected to RP-HPLC analysis using $C_{18}$ column (5 μm, 50×4.6 mm), which was eluted with solvent gradient of 0.1% formic acid/acetonitrile (solvent B) in 0.1% formic acid/$H_2O$ (solvent A): 10-25% from 0 to 10 min; 25% from 10 to 20 min; 25-45% from 20 to 45 min; 45-100% from 45 to 70 min. The fractions of the peak (retention time, 51 min) were collected, and reduced with sodium borohydride as described before (Sok et al, Arch. Biochem. Biophys. 277 (1990) 86-93). The reduction products, after ethyl acetate extraction at pH 3.0, were subjected to SP-HPLC equipped with silica gel column (4 μm, 150×3.9 mm, Waters, USA), which was eluted (1 ml/min) with n-hexane/isopropyl alcohol/acetic acid (100:1: 0.1). Finally, the identification of the product was performed by coinjection with each standard compound, 13(S)-hydroxyoctadecadienoic acid (HODE) or 9 (S)-HODE.

Results

Figure 2:
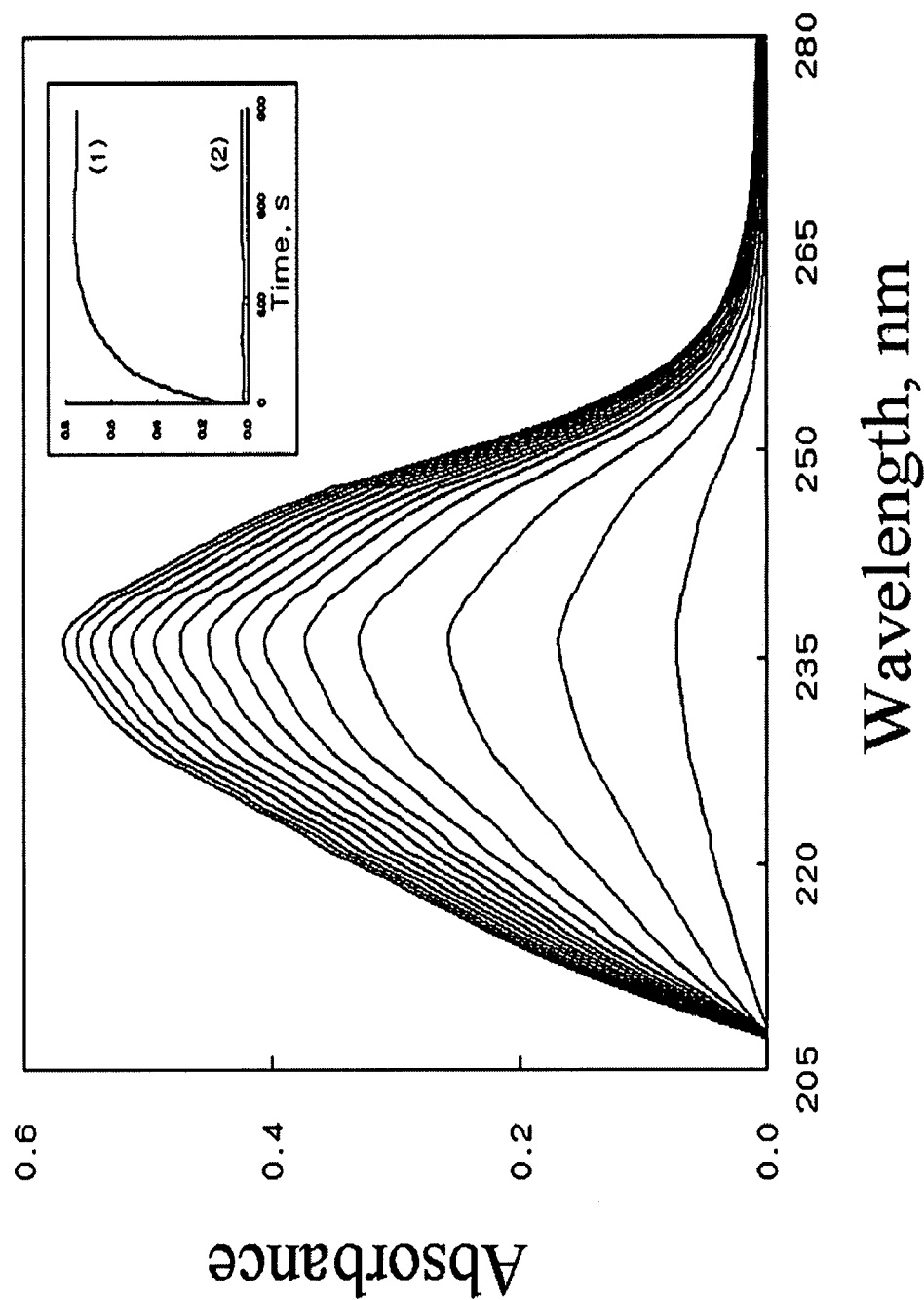
FIG. 2 is a graph showing absorbance degree after treatment of lipoxygenase with 1-linoleoyl lysophosphatidylcholine.

When soybean LOX-1 was incubated with linoleoyl-lysoPC as substrate in 50 mM borax buffer (pH 9), the UV spectral change corresponding to the enzymatic hydroperoxidation of linoleoyl-lysoPC (100 μM) was observed with a maximal absorbance at 234 nm, consistent with the formation of conjugated dienes (FIG. 2). The nature of the spectral change during the enzyme assay shows that the formation of the oxygenation product was proportional to time up to 3 min (FIG. 2, inset). Beyond 3 min, the oxygenation rate seems to be retarded, suggestive of a gradual deactivation of LOX-1 activity. The lack of absorbance in the 270 to 280 nm region indicates that there is no significant formation of oxodienes during the short incubation time. This shows that soybean LOX-1 oxidized linoleoyl-lysoPC to readily generate corresponding hydroperoxide form, suggesting that linoleoyl-lysoPC can be used as a substrate for soybean LOX-1. Although soybean lysoPC (100 μM), containing 42% linoleoyl-lysoPC, was also found to be oxygenated by LOX-1, it showed a shorter period of linearity in the oxygenation rate under the conditions used.

Figure 3:
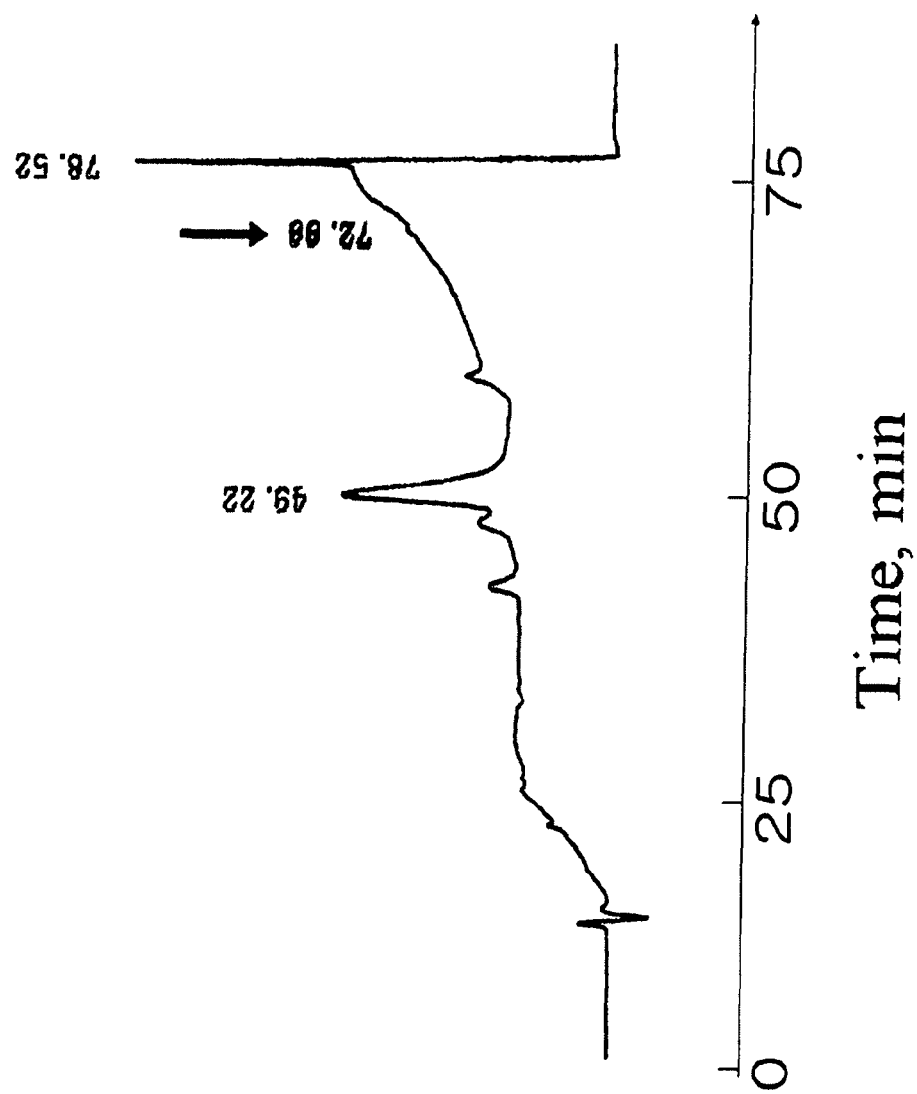
FIG. 3 is an RP-HPLC diagram for products from oxygenation of linoleoyl-lysoPC with LOX-1.
Figure 4:
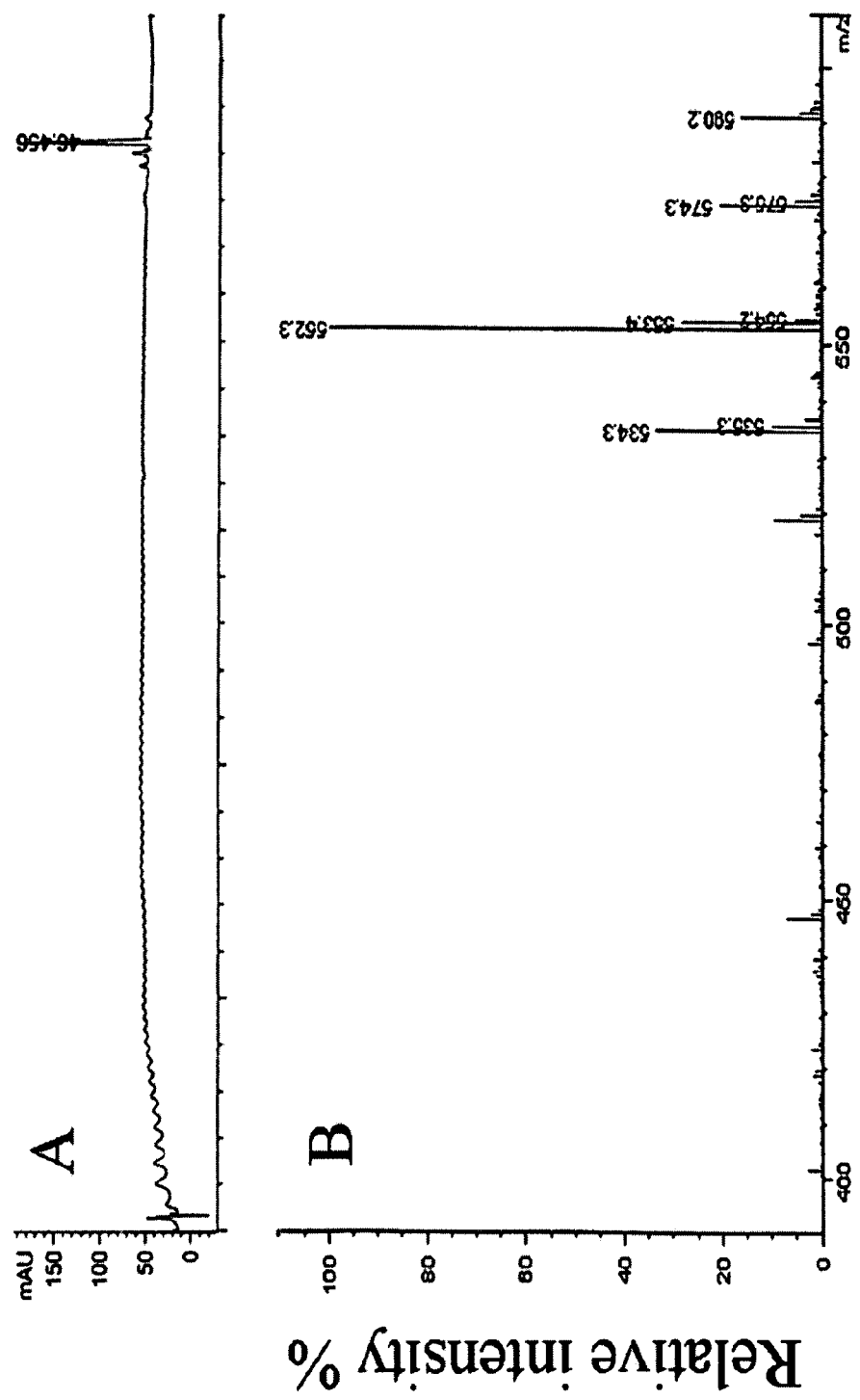
FIGS. 4A and 4B are LC/ESI-MS diagrams for oxygenation products of linoleoyl-lysoPC.

To identify the product from LOX-1-catalyzed oxygenation of linoleoyl-lysoPC, linoleoyl-lysoPC was incubated with LOX-1 in 50 mM borax buffer, pH 9.0, and the lipoxygenation products were partially purified using $C_{18}$ extraction column as described before (M. Pérez-Gilabert, G. A. Veldink, J. F. Vliegenthart, Arch. Biochem. Biophys. 354 (1998) 18-23). When the partially purified products were injected into RP-HPLC column, which was eluted with 45% acetonitrile containing 0.1% formic acid, a major peak (retention time, 49 min), showing an absorbance at 234 nm, was obtained (FIG. 3), in addition to linoleoyl-lysoPC, which appeared as a major peak with a retention time of 72 min (arrow symbol) in a separate experiment monitoring the absorbance at 205 nm. To provide an evidence for the formation of hydroperoxy derivative from linoleoyl-lysoPC, the oxygenation products were subjected to LC/ESI-MS analyses. As demonstrated in FIG. 4A, a major peak (retention time, ca. 47.0 min), the mass spectrum of which corresponds to hydroperoxy derivative of linoleoyl-lysoPC appeared (FIG. 4B); molecular ion at m/z 552.3 ($MH^+$), m/z 574.3 ($[M+Na]^+$) and m/z 590.3 ($[M+K]^+$). Additionally, the peak (elution time, 45.5 min), which appeared as a minor peak, was found to contain hydroxyl derivative of linoleoyl-lysoPC; molecular ion at m/z 536.3 ($MH^+$), m/z 558.3 ($[M+Na]^+$) and m/z 574.3 ($[M+K]^+$).

Another minor peak (elution time, 46 min) was found to contain oxo derivative of linoleoyl-lysoPC as a decomposition product of hydroperoxy linoleoyl-lysoPC (data not shown); molecular ion at m/z 534.3 ($MH^+$), m/z 556.3 ($[M+Na]^+$ and m/z 572.3 ($[M+K]^+$). From this, it is clearly shown that hydroperoxy linoleoyl-lysoPC was obtained as a major oxygenation product during enzymatic oxygenation of the linoleoyl chain of linoleoyl-lysoPC.

Figure 5:
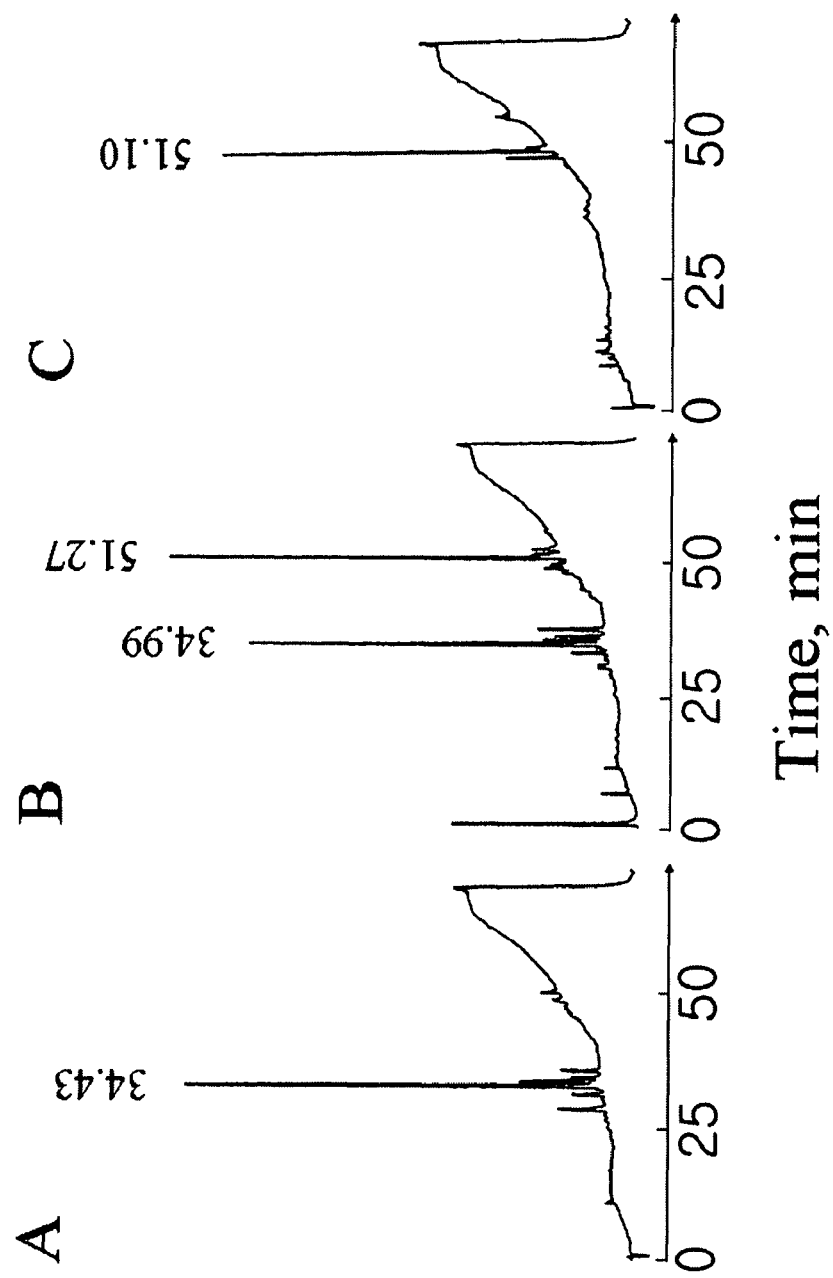
FIGS. 5A-C are RP-HPLC diagrams for products from cholesterol esterase-catalyzed hydrolysis of oxidized linoleoyl-lysoPC.

To establish the position of oxygenation of linoleoyl chain in LOX-1-catalyzed oxygenation of linoleoyl-lysoPC, the hydroperoxy derivative of linoleoyl-lysoPC was hydrolyzed by cholesterol esterase, a hydrolytic enzyme known to hydrolyze 1-monoacyl lysophosphatidylcholine (DiPersio et al, J. Biol. Chem. 265 (1990) 16801-16806; Zschornig et al, J. Lipid. Res. 46 (2005) 803-811), to generate hydroperoxy linoleic acid. For this purpose, the oxygenation products, which were produced from the exposure of linoleoyl-lysoPC to LOX-1 in 50 mM borax buffer (pH 9.0), were further incubated in the presence or absence of cholesterol esterase for 60 min. Then, the oxygenation products were analyzed by RP-HPLC. As exhibited in FIG. 5A, the oxygenated derivative of linoleoyl-lysoPC appeared as a major peak (retention time, 34 min) in the absence of cholesterol esterase. Meanwhile, the inclusion of cholesterol esterase gave rise to another major peak with retention time of ca. 51 min (FIG. 5B), comigrating with hydroperoxy linoleic acid, which was produced from the exposure of linoleic acid to LOX-1 (FIG. 5C).

Figure 6:
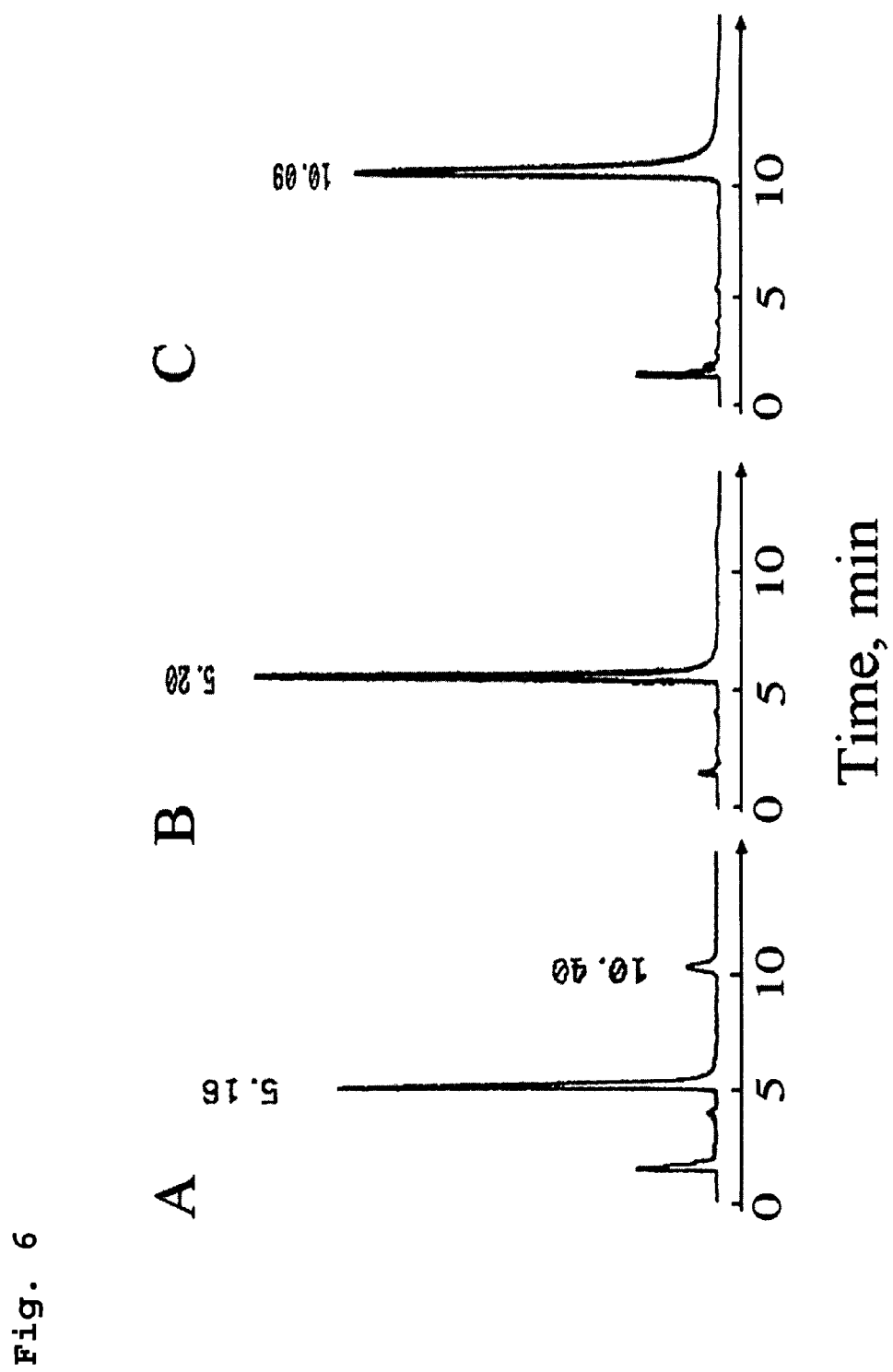
FIGS. 6A-C are SP-HPLC diagrams for determination of oxygenation position of oxidized linoleoyl-lysoPC or soybean lysoPC.

Then, the fraction containing hydroperoxy linoleic acid was collected, reduced with sodium borohydride, and then the reduction products were subjected to SP-HPLC analysis. As displayed in the chromatograms (FIG. 6A), a major peak, showing an absorbance at 234 nm, appeared with an elution time of around 6.5 min, and a minor peak, with elution time of around 13.2 min. In addition, when each peak was coinjected with each standard linoleic acid hydroxide, 13-HODE or 9-HODE, into SP-HPLC column (FIG. 6A), it was found that the major peak migrated with 13-HODE (solid line arrow) while the minor peak did with 9-HODE (dotted line arrow). Based on the area of the peak, the quantitative ratio of 13-HODE to 9-HODE is estimated to be approximately 9:1. From this, it can be suggested that LOX-1 catalyzed oxygenation of linoleoyl-lysoPC selectively at position C-13 of linoleoyl group. In addition, a similar ratio of major peak to minor one was also obtained when LOX-1 was incubated with linoleoyl-lysoPC at pH 7.4 (FIG. 6B), showing that the positional specificity of LOX-1 in oxygenation of linoleoyl-lysoPC was not altered significantly by the change of pH. Separately, a similar result was reproduced when LOX-1 was incubated with soybean lysoPC at both pHs (FIGS. 6C & 6D). Although 9-HODE derivative appeared to be generated in the incubation, a similar amount of 9-hydroperxy derivative was also produced in the incubation of soybean lysoPC with heat-treated lipoxygenase, suggesting that the formation of 9-HODE might be ascribed to non-enzymatic oxygenation caused by the lengthy procedure employing hydrolysis and concentration.

After establishing the conversion of linoleoyl-lysoPC to hydroperoxy derivative of linoleoyl-lysoPC, the optimal condition for the oxygenation of linoleoyl-lysoPC by LOX-1 was investigated in further studies. First, when the effect of pH on the oxygenation of linoleoyl-lysoPC by LOX-1 was examined (FIG. 7), the oxygenation of linoleoyl-lysoPC varied with pH, with the optimal pH range being about 9, slightly different from the optimal pH value reported for oxygenation of linoleic acid by LOX-1. Separately, the effect of detergent on oxygenation of linoleoyl-lysoPC by LOX-1 was examined. However, the oxygenation of linoleoyl-lysoPC was not influenced by Tween 20, contrary to the finding (Schilstra et al, Lipids 29 (1994) 225-231) that the oxygenation of linoleic acid by LOX-1 was enhanced by Tween 20. Even 1-palmitoyl lysoPC (1-3 mM), a native detergent, failed to affect LOX-1-catalyzed oxygenation of linoleoyl-lysoPC.

Figure 8:
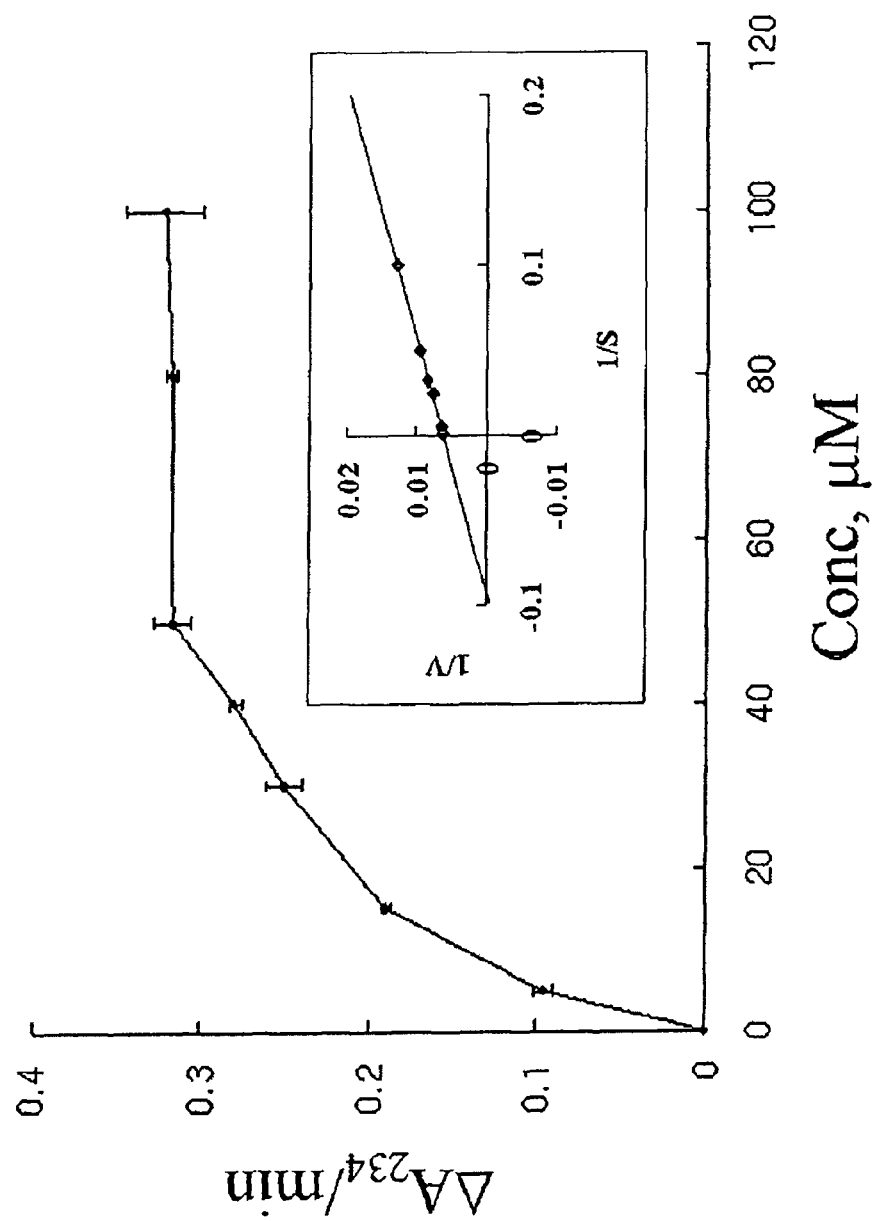
FIG. 8 is an absorbance-concentration graph showing the effect of substrate concentration on oxygenation of linoleoyl-lysoPC by LOX-1.

Next, the effect of linoleoyl-lysoPC concentration on LOX-1-catalyzed oxygenation of linoleoyl-lysoPC was examined. FIG. 8 shows that the enzyme activity followed classical Michaelis-Menten kinetics when linoleoyl-lysoPC concentration was varied. Lineweaver Burke plot for the kinetic data obtained resulted in a linear relationship (FIG. 8, inset), from which the Km and Vm values were estimated to be 12.9 μM and 167.5 units/mg protein, respectively. When the kinetic values for the oxygenation of linoleoyl-lysoPC were compared to those for oxygenation of linoleic acid by LOX-1 (Table 1), the efficiency as substrate was somewhat greater for linoleoyl-lysoPC than for linoleic acid, indicating that linoleoyl-lysoPC might be no less efficient as a substrate for LOX-1 than linoleic acid.

TABLE 1

Kinetic values for oxygenation of linoleoyl-lysoPC or linoleic acid

|  | Km (μM) | Vm (units/mg) | Vm/Km (units/mg/μM) |
|---|---|---|---|
| Linoleic acid | 12 ± 0.70 | 114.3 ± 6.0 | 9.53 ± 0.53 |
| Soybean lysoPC | 16 ± 0.66 | 170.4 ± 10.9 | 10.65 ± 1.01 |
| Linoleoyl-lysoPC | 12.9 ± 1.64 | 167.5 ± 10.4 | 12.98 ± 2.54 |

EXAMPLE 3

Assay of Lipoxygenase with 1-arachidonyl Lysophosphatidylcholine

Materials & Methods

Diarachidonoyl phosphatidylcholine (99%), and 1-arachidonoyl lysophosphatidic acid (99%) were obtained from Avanti Polar Lipid (Alabaster, Ala., USA). Soybean lipoxygenase (Type I-B), phospholipase $A_2$ (honey bee venom), 15-hydroxyeicosatetraenoic acid (HETE), 12-HETE and Tween 20 were purchased from Sigma-Aldrich Corp (St. Louis, Mo., USA). Rabbit reticulocyte 15-lipoxygenase (5,000 units/ml) was obtained from Biomol Inc. (Plymouth Meeting, Pa., USA). Leukocyte 12-lipoxygenase (porcine leukocyte, 1625 units/ml) and other HETE standards were from Cayman Chemical Co. (Ann Arbor, Mich., USA). HPLC solvents were of HPLC grade, and other chemicals were of analytical grade. 1-Arachidonoyl lysophosphatidylcholine (arachidonoyl-lysoPC) was prepared from $PLA_2$-catalyzed hydrolysis of diarachidonoyl phosphatidylcholine as described previously with a slight modification (Pérez-Gilabert et al, Arch. Biochem. Biophys. 354 (1998) 18-23; Barroso et al, J. Chromatogr. B. Analyt. Technol. Biomed. Life. Sci. 814 (2005) 21-28).

Assay of LOX Activities in Oxygenation of Arachidonic Acid or Arachidonoyl-Lysophospholipids Activities of various LOXs were monitored by measuring the increase in absorbance at 234 nm due to the formation of hydroperoxide ($\epsilon_{234}$=25,000 $M^{-1}$ $cm^{-1}$) at 25° C. as described before (Smith et al, J. Biol. Chem. 247 (1972) 1038-1047). One unit is defined as the amount of LOXs that can produce one nanomole of conjugated diene per min. The reaction mixture (500 μl) included reticulocyte LOX (2 units/ml) in 50 mM phosphate buffer (pH 7.4), porcine leukocyte LOX (1 unit/ml) in 100 mM phosphate buffer (pH 7.5) containing 5 mM EDTA and 0.03% Tween 20, or soybean LOX-1 (2.5 units/ml) in 50 mM borax buffer (pH 9.0) at 25° C. The reactions were started by including each substrate (100 μM) into the above reaction mixture.

Determination of Kinetic Values in LOX-Catalyzed Oxygenation of Arachidonic Acid or Arachidonoyl Lysophospholipids Reticulocyte LOX (2 units/ml), leukocyte LOX (1 units/ml) or soybean LOX-1 (2.5 units/ml) was incubated with each arachidonoyl derivative substrate of various concentrations as described above. The values of kinetic parameters were obtained according to Lineweaver Burke plot analyses as described before (Barroso et al, J. Chromatogr. B. Analyt. Technol. Biomed. Life. Sci. 814 (2005) 21-28).

Separation of Oxygenation Products of Arachidonoyl Lysophospholipids by RP-HPLC

Oxygenation of arachidonoyl-lysoPC was started by including soybean LOX-1 (10 units/ml) in 150 µl of 50 mM borax buffer (pH 9.0) containing arachidonoyl-lysoPC (100 µM), or including leukocyte LOX (1.5 units/ml) in 150 µl of 50 mM phosphate buffer (pH 7.4) containing arachidonoyl-lysoPC (100 µM). After 10 min, the reaction products were injected into RP-HPLC system (Hitachi L-7100 pump, Japan), equipped with ZORBAX Eclipse XDB $C_{18}$ column (5 µm, 50×4.6 mm, Agilent Technologies, USA), which was eluted at a flow rate of 1 ml/min with a gradient system of solvent B (acetic acid/acetonitrile/$H_2O$; 0.05:80:20) in solvent A (methanol/$H_2O$; 10:90): 30-75% from 0 to 50 min. Separately, arachidonoyl-lysoPA (100 µM) was oxygenated by soybean LOX-1 or leukocyte LOX as described above, and the oxygenation products were analyzed by HPLC with a gradient solvent system of solvent B (acetic acid/acetonitrile/$H_2O$; 0.05:80:20) in solvent A (methanol/$H_2O$; 10:90): 50-75% from 0 to 50 min.

Determination of Position Specificity in LOX-Catalyzed Oxygenation of Arachidonoyl Lysophospholipids Arachidonoyl-lysoPA (400 µM) or arachidonoyl-lysoPC (400 µM) was incubated with soybean LOX-1 (10 units/ml) or leukocyte LOX (30 units/ml) in 2 ml of the respective incubation buffer described above. After 30 min incubation, the reaction was stopped by the addition of sodium borohydride to reduce hydroperoxy compounds to their corresponding alcohols, which were subjected to alkaline hydrolysis. After 30 min incubation at 60° C. under $N_2$, the mixture was subjected to lipid extraction as described previously (Leon et al, J. Agric. Food. Chem. 52 (2004) 1207-1211). Finally, the lipid extract was analyzed by SP-HPLC system equipped with silica gel column (4 µm, 150×3.9 mm, Waters, USA), which was eluted (1 ml/min) with n-hexane/isopropyl alcohol/acetic acid (100:1:0.05). The identification of hydrolysis products was carried out in comparison with each standard compound, 15-hydroxyeicosatetraenoic acid (HETE) or 12-HETE.

Determination of Stero-Selectivity in LOX-Catalyzed Oxygenation of Lysophospholipids 15-HETE, prepared by SP-HPLC as described above, was subjected to the analysis by chiral phase HPLC equipped with chiralcel OD-H column (250×4.6 mm, 5 µm, Daicel Chemical Industries, LTD, Japan) with the solvent system of n-hexane/isopropyl alcohol/trifluoroacetic acid (100:3:0.05) for the separation of the R and S enantiomers of 15-HETE. Separately, the stereochemistry of 12-HETE was analyzed using the solvent system of n-hexane/isopropyl alcohol/trifluoroacetic acid (100:2:0.05) as described above. The flow rate of the solvent system was 0.5 ml per min, and the effluent was monitored at 234 nm (Axelrod et al, Methods Enzymol. 71 (1981) 441-451).

LC/ESI-MS Analysis

LC/ESI-MS analysis was performed using a MSDI spectrometer (HP 1100 series LC/MSD, Hewlett Packard, USA) equipped with ZORBAX Eclipse XDB $C_{18}$ column (5 µm, 50×4.6 mm, Agilent Technologies, USA), which was eluted (0.8 ml/min) with an isocratic system of solvent B (acetate/acetonitrile/$H_2O$; 0.05:80:20) in solvent A (methanol/$H_2O$; 10:90): 45% from 0 to 15 min for arachidonoyl-LPC, and 60% from 0 to 30 min for arachidonoyl-LPA. The products were monitored by UV detection at 234 or 268 nm, or by ESI-MS system using positive-ion scan mode or selected ion monitoring (SIM) mode.

Identification of Leukotriene Derivatives Generated from Oxygenation of Arachidonoyl Lysophospholipids Arachidonoyl-lysoPC (200 µM) or arachidonoyl-lysoPA (200 µM) was incubated with soybean lipoxygenase (20 units/ml) in 40 ml of 5 mM borax buffer (pH 9.0) at 4° C. for 1 hr. Then, the reaction mixture, after pH adjustment to pH 7.0, was further incubated with leukocyte LOX (30 units/ml) or soybean LOX-1 (200 units/ml). After further incubation for 2 h at room temperature, the mixture was acidified to pH 3, and passed through $C_{18}$ extraction column (1×3 cm). Finally, the oxidized products were eluted by methanol, and concentrated under $N_2$ for the analysis by LC/ESI-MS as described above. Separately, arachidonoyl-lysoPC or arachidonoyl-lysoPA was initially exposed to soybean lipoxygenase (40 units/ml) at pH 9.0, and then additional soybean LOX-1 at pH 7.0 as ascribed above. The products were reduced, hydrolyzed and compared with 8(S), 15(S)-DHETE standard in RP-HPLC.

Results

Figure 9:
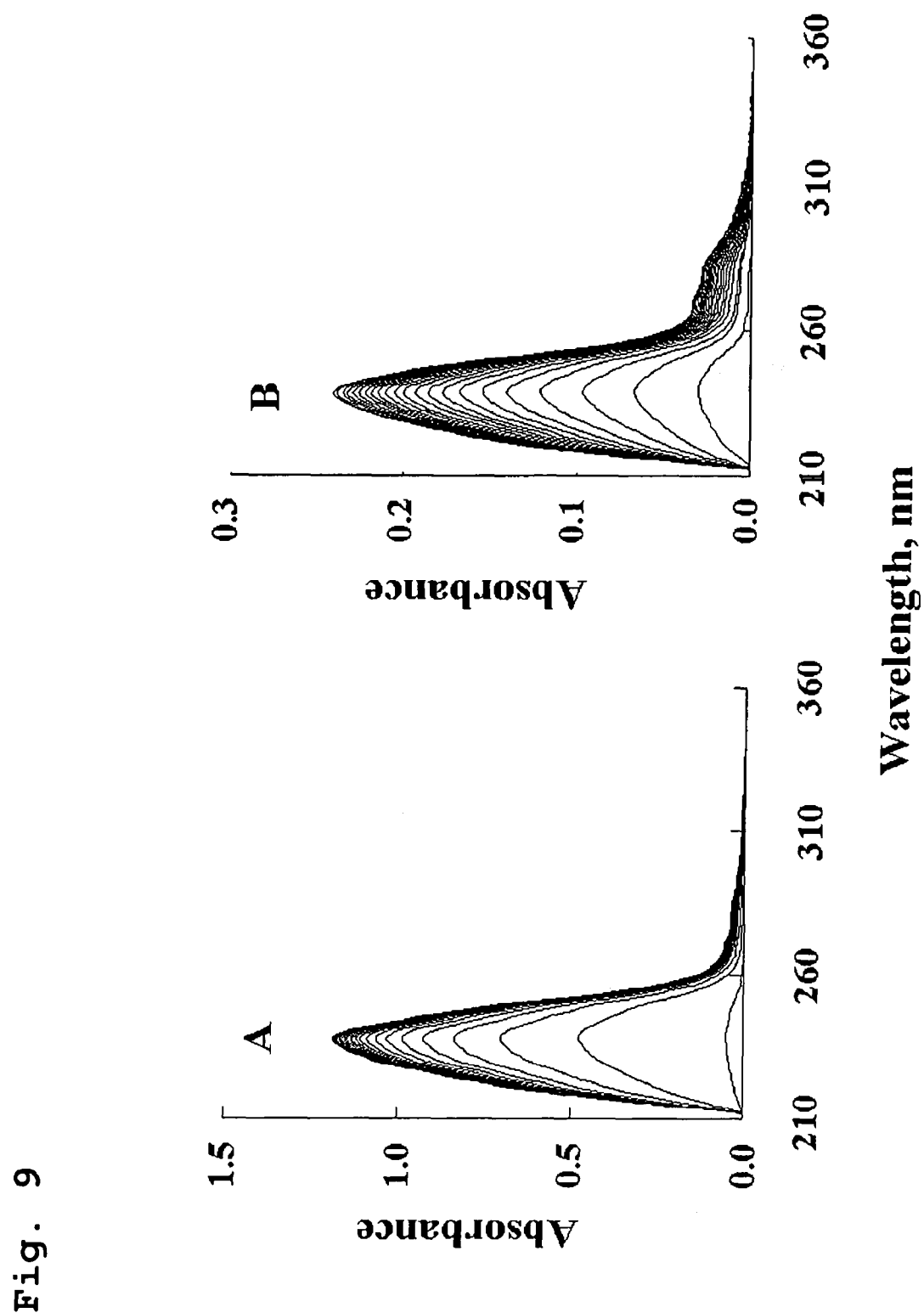
FIGS. 9A and 9B are graphs showing a change of UV spectra during oxygenation of arachidonoyl-lysoPC by soybean LOX-1 or leukocyte LOX.
Figure 10:
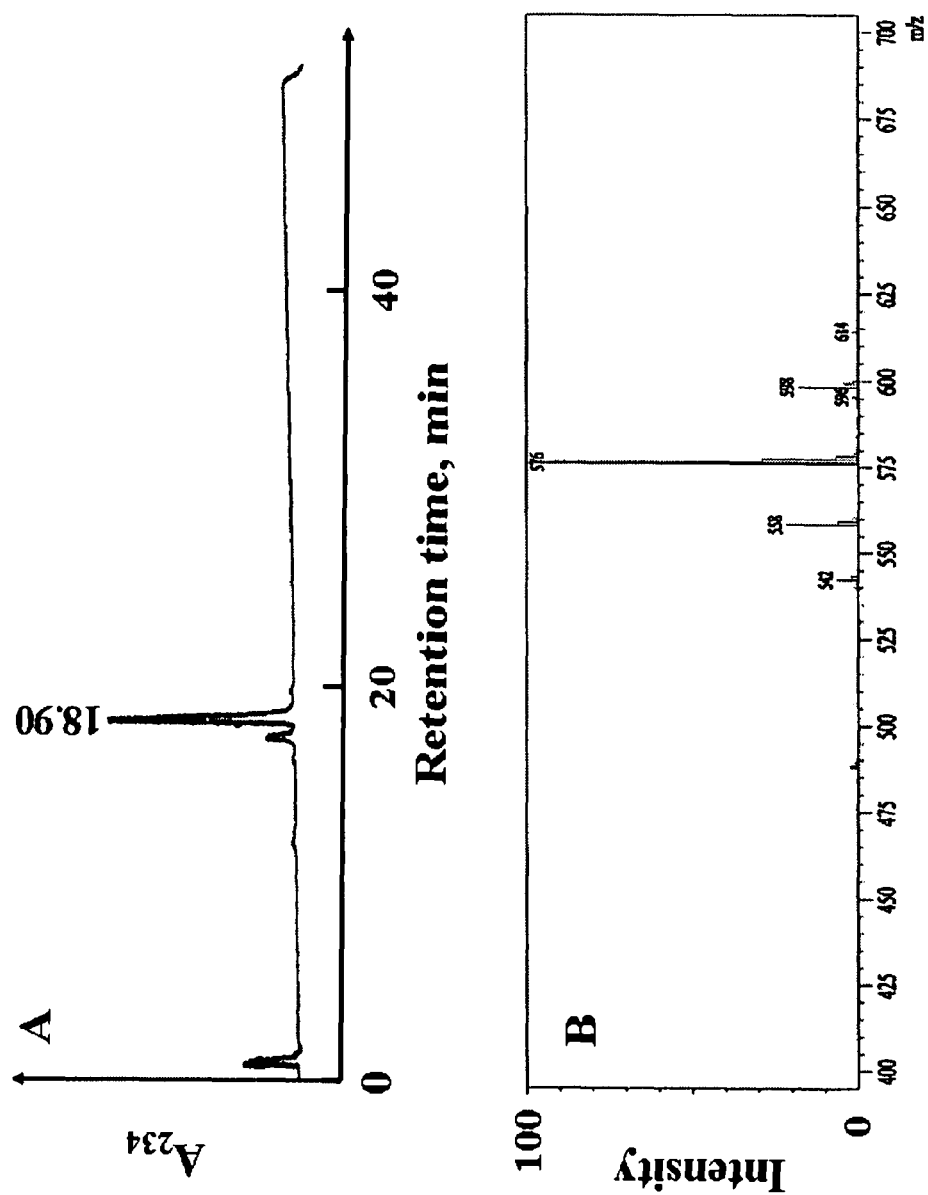
FIGS. 10A and 10B are LC/ESI-MS diagrams for products from oxygenation of arachidonoyl-lysoPC by soybean LOX-1.

LOX-Catalyzed Conversion of Arachidonoyl-LysoPC to Hydroperoxy Eicosatetraenoyl-LysoPC To determine whether arachidonoyl lysophospholipids can be utilized as efficient substrates for lipoxygenases, the oxygenation of arachidonoyl-lysoPC or arachidonoyl-lysoPA by lipoxygenases was examined. First, soybean LOX-1 was incubated with arachidonoyl-lysoPC (100 µM) in 50 mM borax buffer (pH 9) at 25° C., and the UV absorption spectral change was monitored. As shown in FIG. 9A, the exposure of arachidonoyl-lysoPC to soybean LOX-1 caused the time-dependent increase of absorption at 234 nm, consistent with the formation of conjugated dienes during enzymatic lipoxygenation of arachidonoyl-lysoPC. Likewise, a similar change of UV spectrum, indicative of the formation of conjugated dienes, was also observed when arachidonoyl-lysoPC was incubated with leukocyte LOX in 50 mM phosphate buffer, pH 7.4 (FIG. 9B). These show that arachidonoyl-lysoPC can be readily oxygenated as a useful substrate for soybean LOX-1 as well as leukocyte LOX. To identify the products from oxygenation of arachidonoyl-lysoPC, the products from the exposure of arachidonoyl-lysoPC to soybean LOX-1 were partially purified using $C_{18}$ extraction column, and the partially-purified products were subjected to RP-HPLC, which was monitored at 234 nm. FIG. 10A shows that a peak with a retention time of 19 min appeared as a predominant product. When the compound from the major peak was subjected to LC/ESI-MS analysis (FIG. 10B), it was found to show the mass spectrum characteristic of the compound corresponding to hydroperoxy derivative of arachidonoyl-lysoPC; molecular ion at m/z 576 ($MH^+$), m/z 598 ($[M+Na]^+$) and m/z 614 ($[M+K]^+$). Therefore, it can be suggested that hydroperoxyeicosatetraenoyl-lysoPC was obtained as a major oxygenation product during soybean LOX-1-catalyzed oxygenation of arachidonoyl-lysoPC. The same result was also obtained when the oxygenation products from the incubation of arachidonoyl-lysoPC with leukocyte LOX were subjected to LC/ESI-MS analyses (data not shown).

Determination of Position- and Stereo-Selectivity in Oxygenation of Arachidonoyl-LysoPC To establish the position of oxygenation of arachidonoyl chain in arachidonoyl-lysoPC, hydroperoxyeicosatetraenoyl-lysoPC was subjected to $NaBH_4$ reduction, followed by saponification in alkaline medium, to afford hydroxyeicosatetraenoic acid, which was further purified by SP-HPLC. When the chromatographic behavior of the purified hydroxyeicosatetraenoic acid was compared to that of 12-HETE or 15-HETE as a standard compound in SP-HPLC (FIG. 11A), it was found that the major peak with a retention time of around 12.5 min migrated with 15-HETE (solid line arrow), indicating that soybean LOX-1 oxygenated arachidonoyl-lysoPC at C-15 to generate 15-HPETE derivative of lysoPC. Similarly, when the position of oxygenation of arachidonoyl chain in leukocyte LOX-catalyzed oxygenation of arachidonoyl-lysoPC was determined (FIG. 11B), it was found that the predominant product (elution time, ca. 3.2 min) migrated with 12-HETE (dotted line), and the minor one ($\leq 5\%$) with elution time of approximately 12.5 min behaved like 15-HETE, suggesting that leukocyte LOX catalyzed the oxygenation of arachidonoyl-lysoPC mainly at C-12 of arachidonoyl group.

Taken together, it can be suggested that arachidonoyl-lysoPC was oxygenated by soybean LOX-1 mainly at C-15, and by leukocyte LOX mainly at C-12, supporting the notion that the positional specificity of soybean LOX-1 or leukocyte LOX in oxygenation of arachidonoyl-lysoPC follows that for the oxygenation of arachidonoyl group. In related studies, the stereo-selectivity in the oxygenation of arachidonoyl-lysoPC was analyzed by chiral phase HPLC. When 15-HETE, which was obtained as described in FIG. 11A, was subjected to chiral phase HPLC analysis, it was found that the major part of 15-HETE (retention time, 42 min) migrated with 15(S)-HETE (FIG. 12A). Likewise, 12-HETE, prepared from the incubation of arachidonoyl-lysoPC with leukocyte LOX (FIG. 11B), was subjected to chiral phase HPLC analysis, and most of 12-HETE (retention time, 25 min) was found to migrate with 12(S)-HETE (FIG. 12B). Thus, both LOXs express a common stereo-selectivity by generating the S form as a predominant enantiomer in oxygenation of arachidonoyl-lysoPC.

Figure 13:
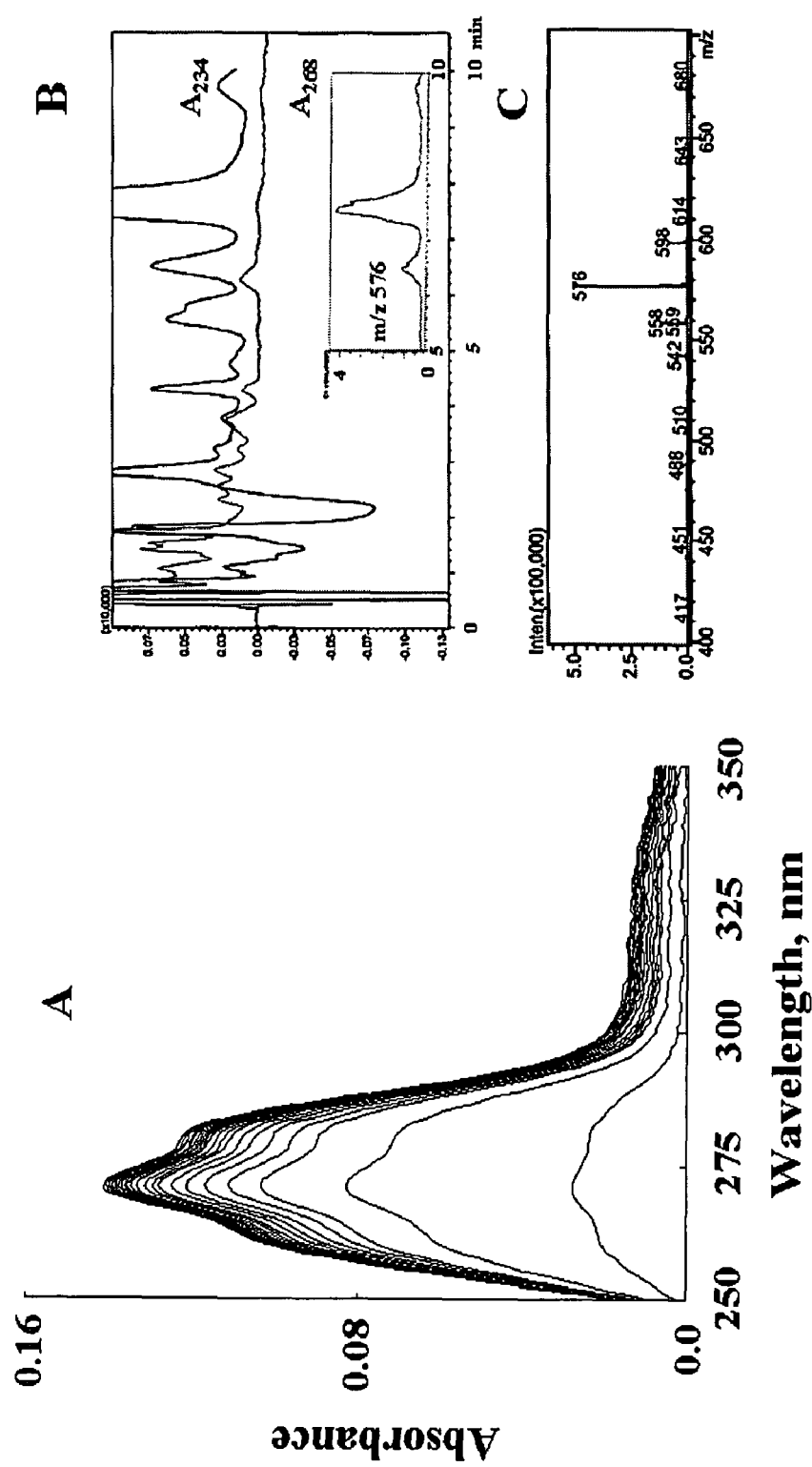
FIGS. 13A-C are graphs that analyze products from the sequential of arachidonoyl-lysoPC to soybean LOX-1 and leukocyte LOX.

Enzymatic Conversion of 15-hydroperoxyeicosatetraenoyl-lysoPC to Dihydroxyeicosatetraenoyl-LysoPC Noteworthy, during the extended incubation of arachidonoyl-lysoPC with leukocyte LOX, a particular UV spectrum with a maximal absorption around 268 nm appeared, in addition to the UV spectrum exhibiting a maximal absorbance at 234 nm (FIG. 9B). Such a UV spectral change, showing a maximal absorption at 268 nm, was more remarkable in the oxygenation by leukocyte LOX rather than soybean LOX-1. In a further study employing differential spectrophotometric analysis, the product from the exposure of arachidonoyl-lysoPC to leukocyte LOX was found to exhibit the UV spectrum with a maximum absorption at 268 nm and shoulders at 258 nm and 290 nm, characteristic of conjugated triene structure (data not shown). These indicate that a conjugated triene derivative of lysoPC is being produced during the oxygenation of arachidonoyl-lysoPC by leukocyte LOX. To prove that the conjugated triene derivative was derived from the primary oxygenation product of arachidonoyl-lysoPC, arachidonoyl-lysoPC was exposed sequentially to soybean LOX-1 and leukocyte LOX. For this purpose, arachidonoyl-lysoPC was first exposed to soybean LOX-1 in borate buffer (pH 9.0) to maximally produce 15-hydroperoxyeicosatetraenoic acid (15-HPETE) derivative of lysoPC, and then the mixture, after the pH adjustment to pH 7.0, was further incubated with leukocyte LOX, which is well known to convert 15-HPETE to dihydroxyeicosatetraenoic acids with the conjugated triene (Brash et al., *Adv Prostaglandin Thromboxane Leukot Res* 17, 75-77). As exhibited in the differential spectrophotometric analysis (FIG. 13A), the sequential exposure of arachidonoyl-lysoPC to soybean LOX-1 and leukocyte LOX led to a remarkable increase in the absorbance at 268 nm with shoulders at 259 nm and 279 nm, indicating that the compound of conjugated triene structure was derived from 15-hydroperoxyeicosatetraenoyl-lysoPC, the hydroperoxide form of arachidonoyl-lysoPC. Thus, arachidonoyl-lysoPC can be suggested to have been oxygenated by soybean LOX-1 to produce 15-hydroperoxyeicosatetraenoyl-lysoPC, which is in turn converted to the conjugated triene derivative in the presence of leukocyte LOX. Subsequently, we turned to the identification of the oxygenation product, which was produced during the sequential exposure of arachidonoyl-lysoPC to soybean LOX-1 and leukocyte LOX. The oxygenation products were partially purified on $C_{18}$ column, and then subjected to LC/MS analyses. FIG. 5B indicates that a peak (retention time, 7.7 min), containing 15-hydroperoxyeicosatetraenoyl-lysoPC, appeared while monitored at 234 nm (FIG. 13B, upper line), and a peak (retention time, 6.2 min) appeared when monitored at 268 nm (FIG. 13B, downer line). The peak (retention time, 6.2 min) in the downer line was observed to contain a compound showing a UV spectrum with a maximal wavelength at 268 nm. In a SIM monitoring (FIG. 13B, inset), the compounds of the peak (retention time, 7.7 min) in upper line and the peak (retention time, 6.2 min) in downer line were observed to possess the same molecular ion at m/z 576 ($MH^+$). Finally, when the compound, showing the UV spectrum of conjugated triene structure, was analyzed by LC/ESI-MS, it was observed that the compound contained molecular ions corresponding to dihydroxyeicosatetraenoyl-lysoPC (FIG. 13C); molecular ions at m/z 576 ($MH^+$), m/z 598 ($[M+Na]^+$) and m/z 614 ($[M+K]^+$).

LOX-Catalyzed Oxygenations of Arachidonoyl-LysoPA

Figure 11:
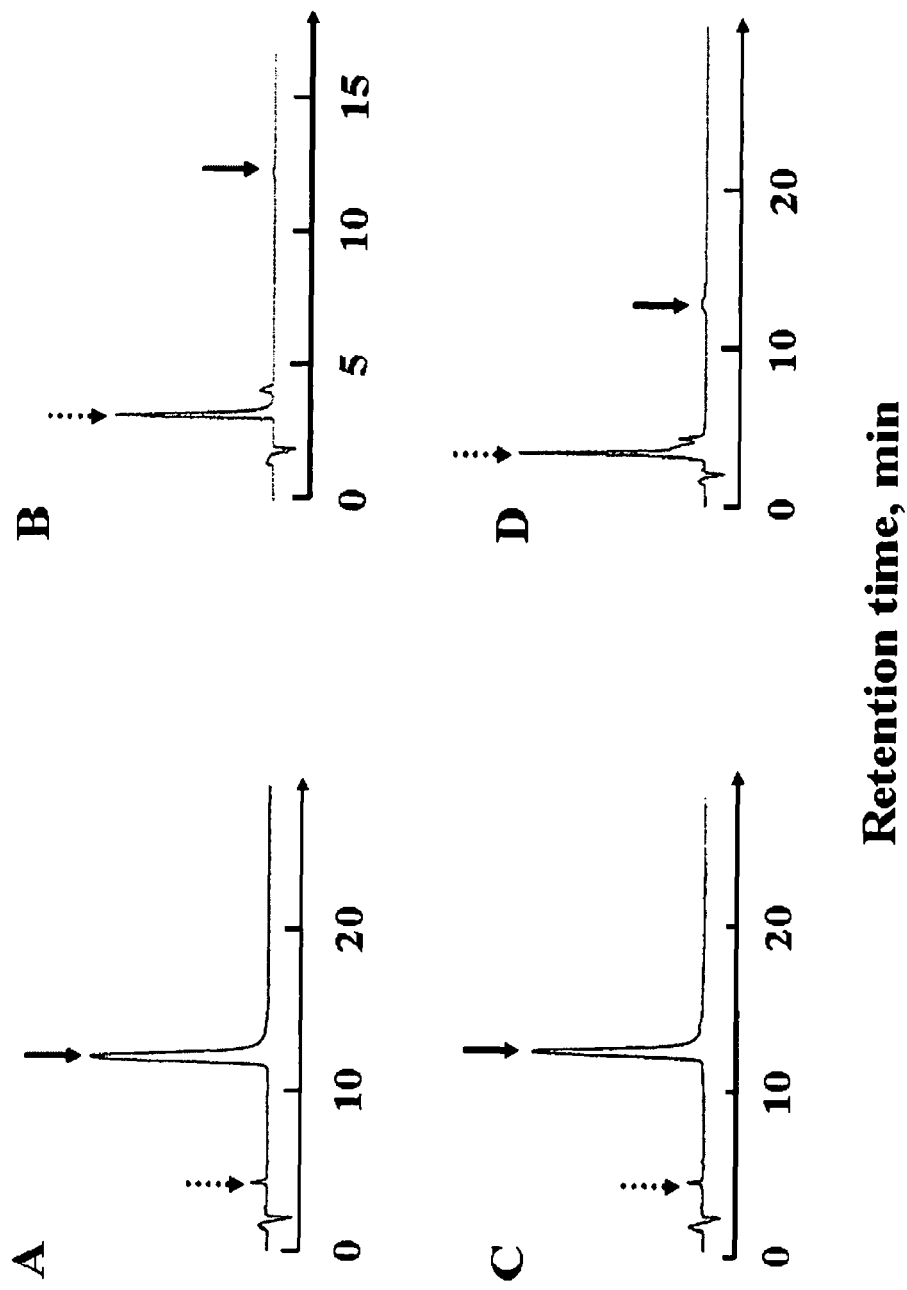
FIGS. 11A-D are SP-HPLC diagrams for products from oxygenation of arachidonoyl-lysoPC by soybean LOX-1 and leukocyte LOX.
Figure 12:
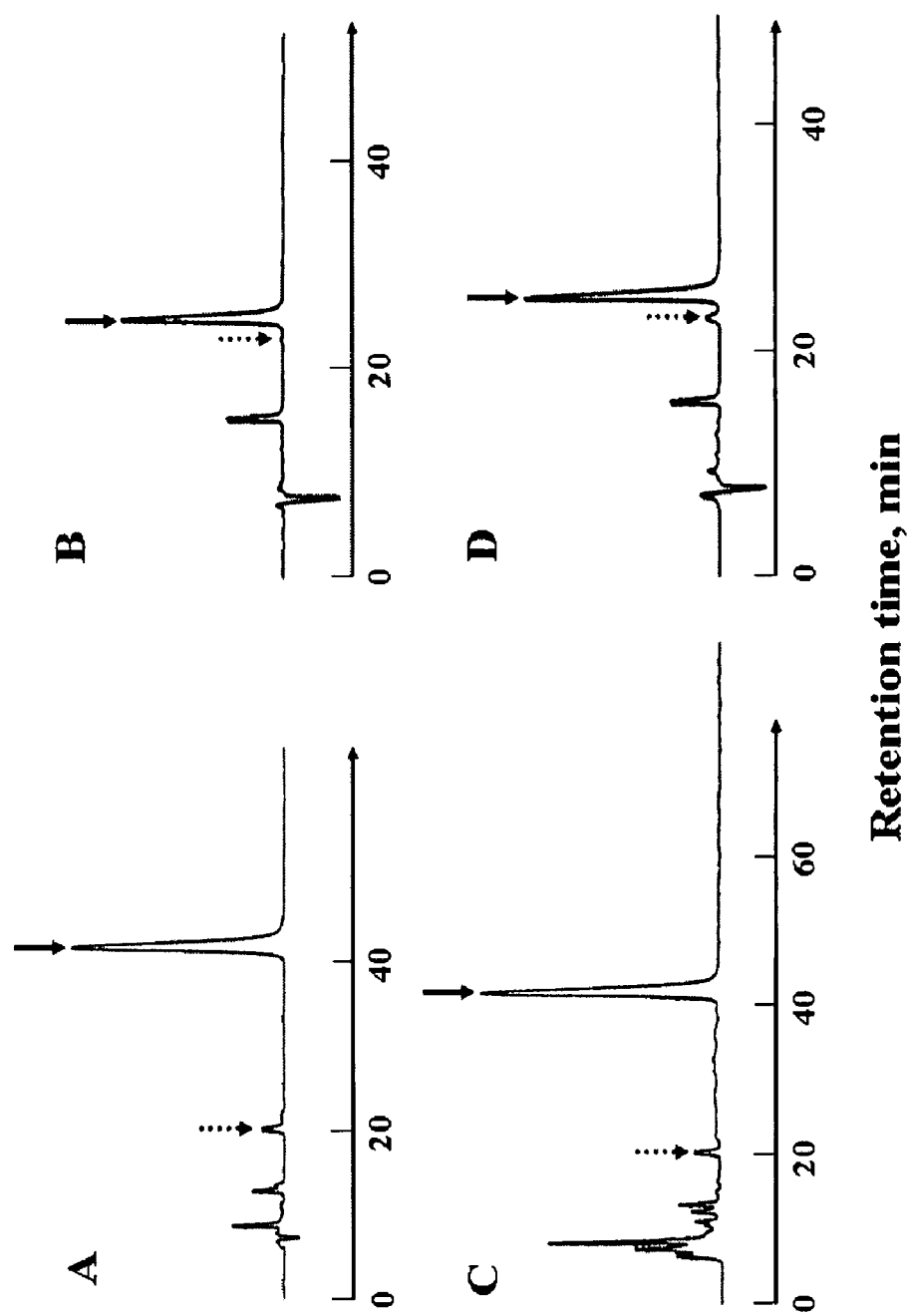
FIGS. 12A-D are chiral-phase HPLC diagrams for HETE derived from oxygenation of arachidonoyl-lysoPC and arachidonoyl-lysoPA by lipoxygenases.
Figure 14:
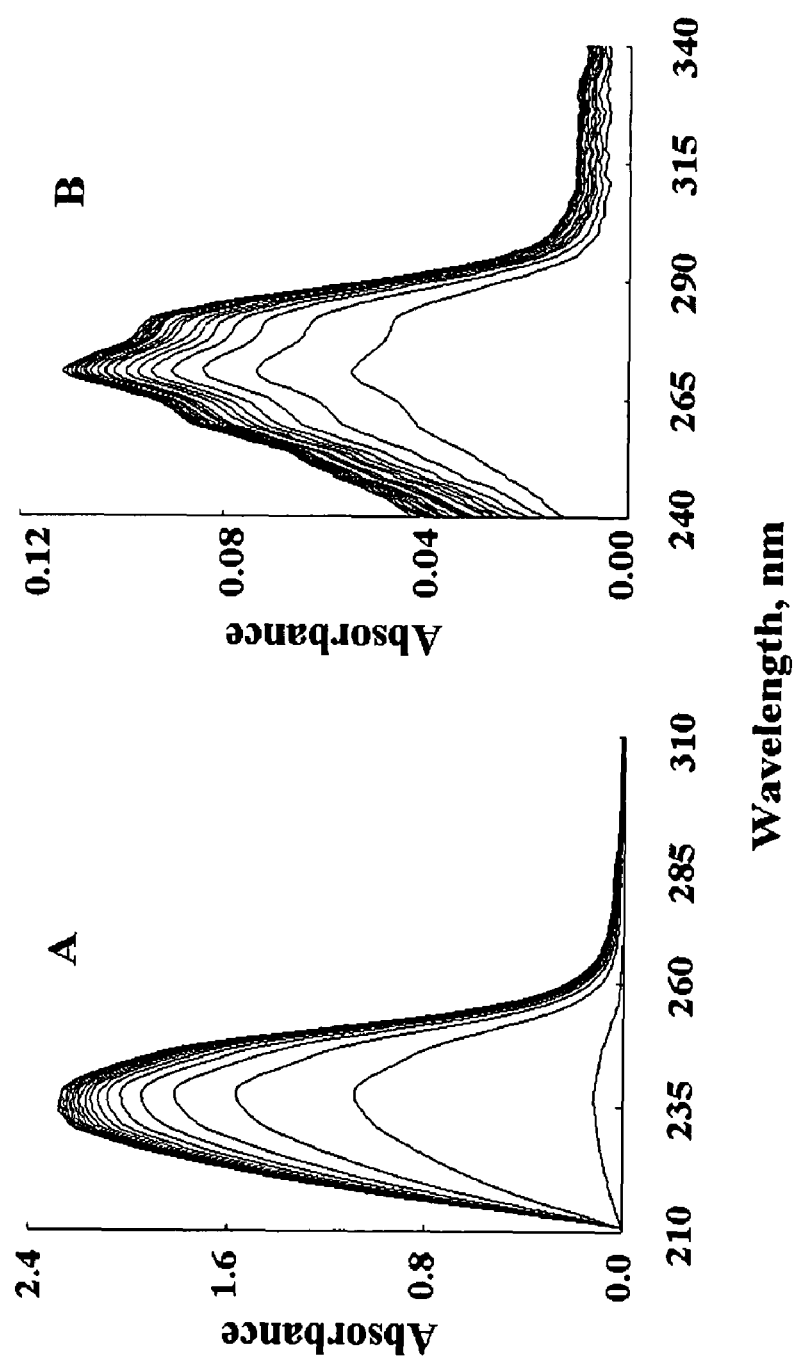
FIGS. 14A and 14B are diagrams showing a change of UV spectra during oxygenation of arachidonoyl-lysoPA by soybean LOX-1.

The lipoxygenation of arachidonoyl-lysoPA by soybean LOX-1 or leukocyte LOX was investigated. When arachidonoyl-lysoPA (200 µM) was incubated with soybean LOX-1 as described above, the UV spectral change with a maximal absorbance at 234 nm was found (FIG. 14A), similar to the finding with arachidonoyl-lysoPC. Also, a similar result was obtained when arachidonoyl-lysoPA (200 µM) was incubated with leukocyte LOX (data not shown). Thus, it can be suggested that soybean LOX-1 as well as leukocyte LOX efficiently converted arachidonoyl-lysoPA to the respective monohydroperoxide form. To support the above notion, the oxygenation products of arachidonoyl-lysoPA were subjected to LC/ESI-MS analysis, and the mass spectrum of the product from the major peak was found to contain characteristic ions indicative of the compound corresponding to hydroperoxy derivative of arachidonoyl-lysoPA; molecular ion at m/z 490.3 ($MH^+$), m/z 512.3 ($[M+Na]^+$) and m/z 528.3 ($[M+K]^+$). Thus, it is suggested that 15-hydroperoxyeicosatetraenoyl-lysoPA was obtained as a major oxygenation product in soybean LOX-1-catalyzed oxygenation of arachidonoyl-lysoPA. The same result was also obtained when arachidonoyl-lysoPA was oxygenated with leukocyte LOX (data not shown). In a separate experiment, where the position of oxygenation of arachidonoyl chain in arachidonoyl-lysoPA was determined, it was found (FIG. 11C) that HETE (retention time, 12.5 min), derived from oxygenation of arachidonoyl-lysoPA by soybean LOX-1, migrated with 15-HETE standard (solid line arrow). Meanwhile, HETE (retention time, 3.2 min), derived from oxygenation of arachidonoyl-lysoPA by leukocyte LOX, migrated with 12-HETE standard (FIG. 11D). Thus, it can be inferred that the positional specificity of soybean LOX-1 or leukocyte LOX in oxygenation of arachidonoyl-lysoPA is the same as that for the oxygenation of arachidonoyl-lysoPC. Subsequently, the stereo-selectivity in the oxygenation of arachidonoyl-lysoPA was analyzed by chiral phase HPLC. As shown in FIG. 12, 15-HETE, which was derived from oxygenation of arachidonoyl-lysoPA by soybean LOX-1 (FIG. 11C), behaved like standard 15(S)-

HETE (FIG. 12C). Meanwhile, 12-HETE, derived from the incubation of arachidonoyl-lysoPA with leukocyte LOX (FIG. 11D), was found to behave like 12(S)-HETE (FIG. 12D). Thus, both enzymes seem to exhibit a common stereoselectivity in oxygenation of arachidonoyl-lysoPA. In the related experiment, the prior incubation of arachidonoyl-lysoPA with soybean LOX-1 at pH 9.0, followed by additional inclusion of leukocyte LOX at pH 7.0 (FIG. 14B), rapidly caused the appearance of UV spectrum displaying the maximal absorbance at 271 nm and shoulders at 261 nm and 281 nm, similar to the finding with the sequential exposure of arachidonoyl-lysoPC to soybean LOX-1 and leukocyte LOX. This may support the notion that the conjugated triene derivative was also derived from the exposure of 15-hydroperoxyeicosatetraenoyl-lysoPA to leukocyte LOX. Separately, the double lipoxygenation of arachidonoyl-lysoPA by soybean LOX-1, which is known to show a multiple oxygenation of arachidonic acid, was examined. The exposure of archidonoyl-lysoPA to soybean LOX-1 at pH 9.0, followed by exposure to additional LOX-1 at pH 7.0, also generated the compound displaying UV spectrum with the maximal absorbance at 271 nm, similar to the finding shown in FIG. 14B. To provide an evidence for this, the oxygenation products were reduced with $NaBH_4$, and subjected to alkaline hydrolysis (data not shown). When the hydrolyzed products were analyzed by RP-HPLC employing the UV detection at 268 nm, the compound showing the UV spectrum characteristic of conjugated triene was found to co-elute with 8(S), 15(S)-DHETE standard, which was prepared as described before (Brash et al., Adv Prostaglandin Thromboxane Leukot Res 17, 75-77). In contrast, archidonoyl-lysoPC was not susceptible to the double oxygenation by soybean LOX-1 (data not shown).

Figure 15:
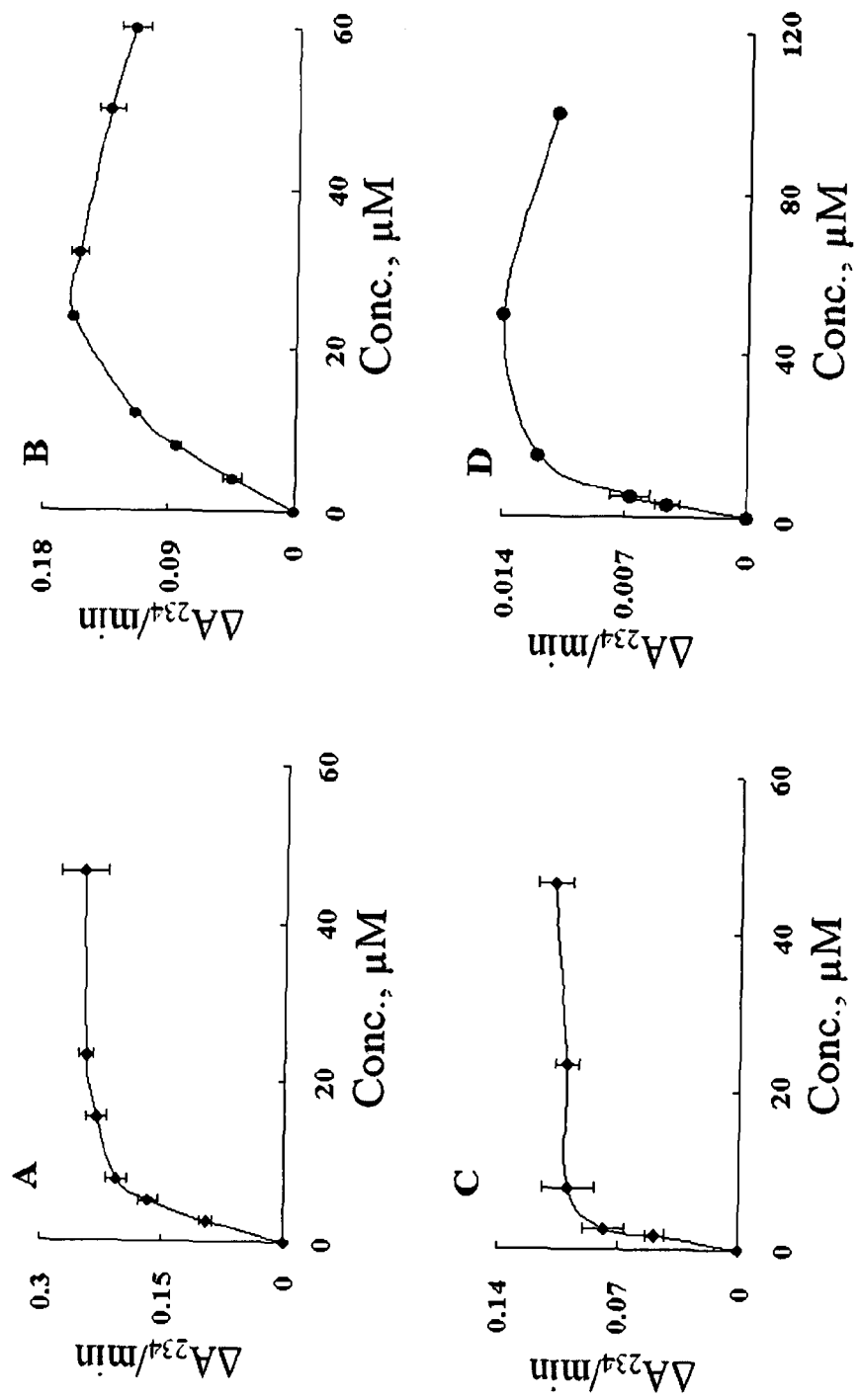
FIGS. 15A-D are graphs showing the effect by substrate concentration on LOX-catalyzed oxygenation of arachidonoyl-lysoPC or arachidonoyl-lysoPA.

Determination of Kinetic Values in LOX-Catalyzed Oxygenation of Arachidonoylated Lipids Subsequently, the effect of substrate concentration on LOX-catalyzed oxygenation of arachidonoyl-lysoPC or arachidonoyl-lysoPA was examined. As demonstrated in FIG. 15, the enzyme activity followed classical Michaelis-Menten kinetics when each enzyme was incubated with arachidonoyl-lysoPC or arachidonoyl-lysoPA at various concentrations. Overall, arachidonoyl-lysoPC (FIGS. 15A & 15C) reached a maximal oxygenation rate at smaller concentrations than arachidonoyl-lysoPA (FIGS. 15B & 15D). In the kinetic study using Lineweaver Burk plot analysis, the Km and Vm values in oxygenation by soybean LOX-1 were estimated to be 5.4 μM and 97.0 units/μg protein, respectively for arachidonoyl-lysoPC, and 15.4 μM and 147.8 units/μg protein, respectively for arachidonoyl-lysoPA, in contrast to 12.4 μM and 92.2 units/μg protein, respectively for arachidonic acid (Table I).

TABLE 2

Kinetic values in oxygenation of arachidonic acid or arachidonoyl-lysophospholipids by soybean LOX-1

|  | Km (μM) | Vm (units/μg) | Vm/Km (units/μg/μM) |
| --- | --- | --- | --- |
| Arachidonic acid | 12.4 ± 3.5 | 92.2 ± 3.0 | 7.4 ± 0.3 |
| Arachidonoyl-lysoPA | 15.4 ± 1.7 | 147.8 ± 2.3 | 9.6 ± 1.0 |
| Arachidonoyl-lysoPC | 5.37 ± 1.6 | 97.0 ± 8.2 | 20.4 ± 8.0 |

Thus, the efficacy as substrate of soybean LOX-1 was the greatest with arachidonoyl-lysoPC, followed by arachidonoyl-lysoPA and arachidonic acid. Next, when the kinetic values in the oxygenation by leukocyte LOX were determined (Table 2), the Km and Vm values were 2.6 μM and 199.8 units/mg protein, respectively for arachidonoyl-lysoPC, and 8.6 μM and 33.5 units/mg protein, respectively for arachidonoyl-lysoPA, in contrast to 7.7 μM and 63.2 units/mg protein, respectively for arachidonic acid.

TABLE 3

Kinetic values in oxygenation of arachidonic acid or arachidonoyl-lysophospholipids by leukocyte LOX

|  | Km (μM) | Vm (units/mg) | Vm/Km (units/mg/μM) |
| --- | --- | --- | --- |
| Arachidonic acid | 7.7 ± 1.6 | 63.2 ± 11.9 | 8.2 ± 1.5 |
| Arachidonoyl-lysoPA | 8.6 ± 2.3 | 33.5 ± 2.9 | 4.1 ± 1.2 |
| Arachidonoyl-lysoPC | 2.6 ± 0.2 | 199.8 ± 16.7 | 81.3 ± 2.8 |

Overall, arachidonoyl-lysoPC was found to be more efficient than arachidonic acid or arachidonoyl-lysoPA as substrates for leukocyte LOX, based on the Vm/Km value. It is noteworthy that the efficacy of arachidonoyl-lysoPC as a substrate for leukocyte LOX was approximately 10-fold greater than that of arachidonic acid. In an additional study, the oxygenation of arachidonoyl-lysoPC or arachidonoyl-lysoPA by reticulocyte LOX was examined. Table III indicates that the Vm/Km value of arachidonoyl-lysoPC or arachidonoyl-lysoPA in reticulocyte LOX-catalyzed oxygenation is somewhat greater than that of arachidonic acid, suggesting that arachidonoyl-lysophospholipids may be favorable substrates of reticulocyte LOX-1. Thus, arachidonoyl-PC or arachidonoyl-PA may be utilized as efficient substrates for soybean LOX-1, leukocyte LOX and reticulocyte LOX.

In contrast, the Vm value of arachidonoyl-lysoPC or arachidonoyl-lysoPA in the oxygenation by potato LOX was >100-fold less than that of arachidonic acid.

EXAMPLE 4

Assay of Lipoxygenase with 1-docosahexenoyl-lysophosphatidylcholine

Figure 16:
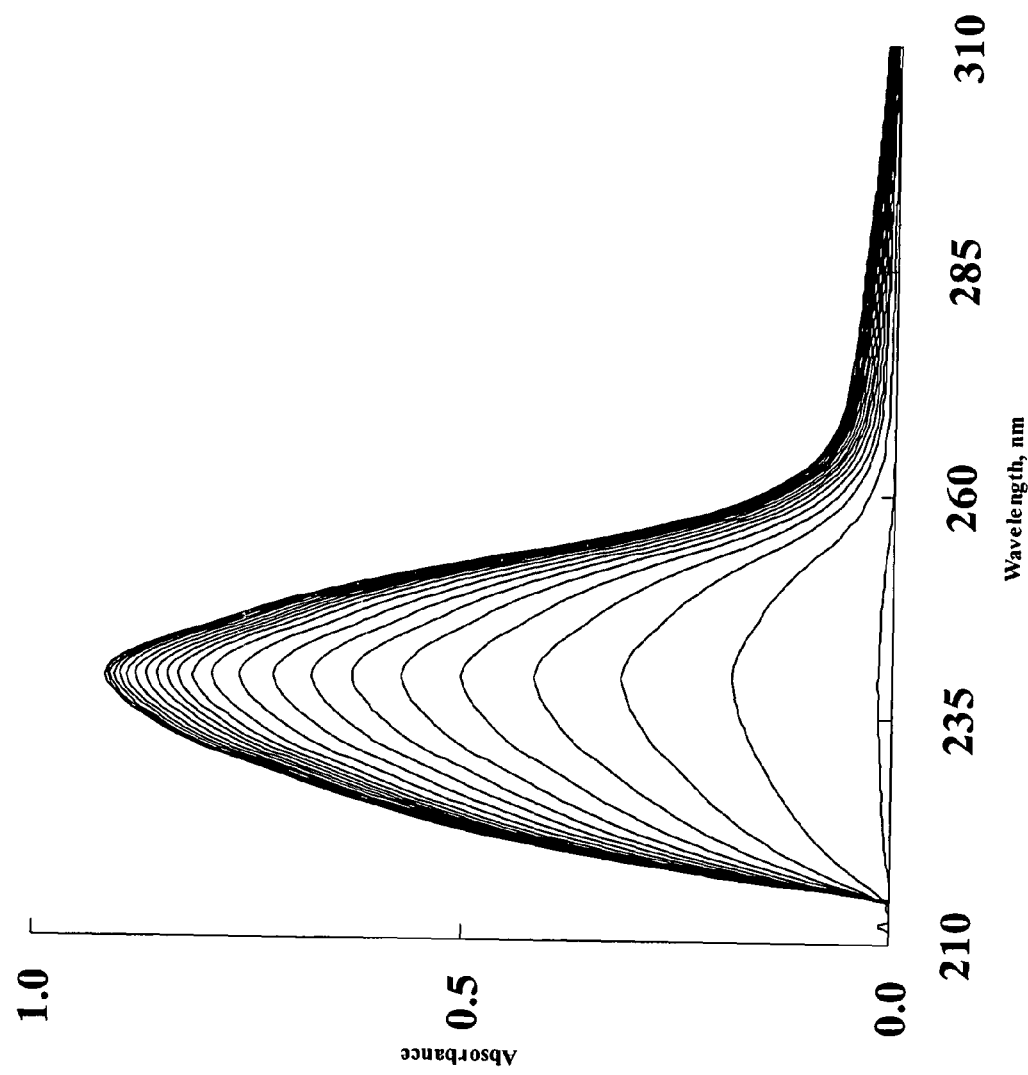
FIG. 16 is a diagram showing a change of UV spectra during oxygenation of docosahexaenol-lysoPC by soybean LOX-1 or leukocyte LOX.
Figure 17:
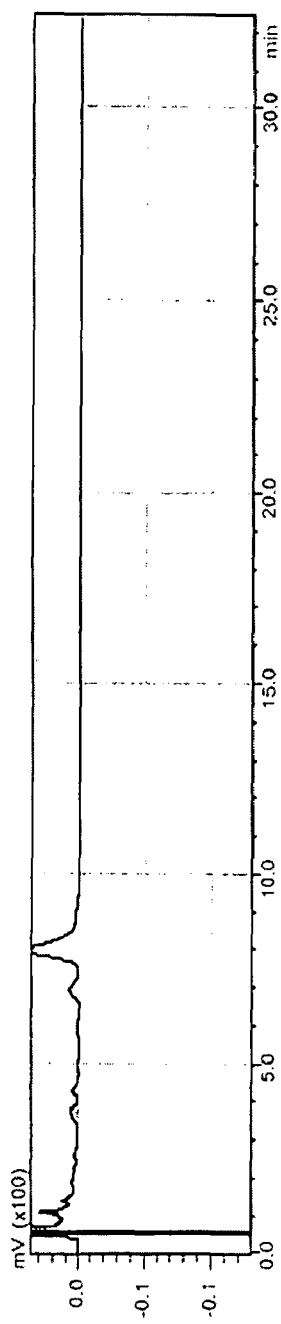
FIG. 17A is an RP-HPLC diagram for products from oxygenation of docosahexaenoyl-lysoPC with LOX-1 and FIG. 17B is an LC/ESI-MS diagram for oxygenation products of docosahexaenoyl-lysoPC.
Figure 17:
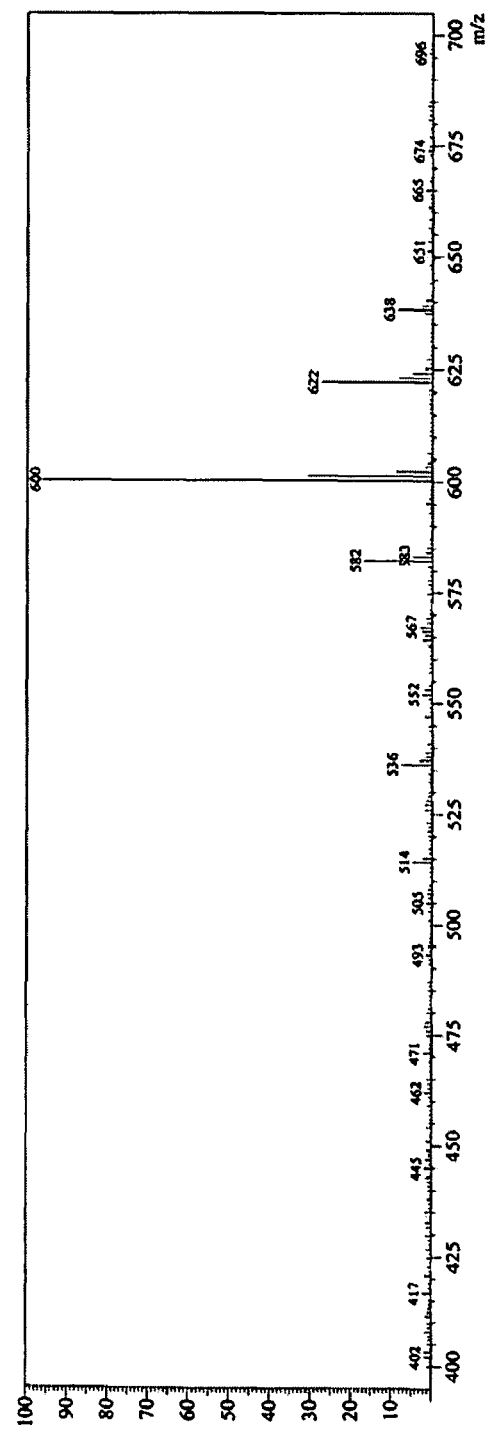

To determine whether 1-docosahexenoyl lysophospholipids could be utilized as efficient substrates for lipoxygenases, the oxygenation of 1-docosahexenoyl-lysoPC or 1-docosahexenoyl-lysoPA by lipoxygenases was examined. First, soybean LOX-1 was incubated with 1-docosahexenoyl-lysoPC (100 μM) in 50 mM borax buffer (pH 9) at 25° C., and the UV absorption spectral change was monitored. As shown in FIG. 16, the exposure of 1-docosahexenoyl-lysoPC to soybean LOX-1 caused the time-dependent increase of absorption at 234 nm, consistent with the formation of conjugated dienes during enzymatic lipoxygenation of 1-docosahexenoyl-lysoPC. To identify the products from oxygenation of 1-docosahexenoyl-lysoPC, the products from the exposure of arachidonoyl-lysoPC to soybean LOX-1 were partially purified using $C_{18}$ extraction column, and the partially-purified products were subjected to RP-HPLC, which was monitored at 234 nm. FIG. 17A shows that a peak with a retention time of 8 min appeared as a predominant product. When the compound from the major peak was subjected to LC/ESI-MS analysis (FIG. 17B), it was found to show the mass spectrum characteristic of the compound corresponding to hydroperoxy derivative of 1-docosahexenoyl-lysoPC. Therefore, it can be suggested that hydroperoxydocosahexenoyl-lysoPC was obtained as a major oxygenation product during soybean LOX-1-catalyzed oxygenation of 1-docosahexenoyl-lysoPC.

Figure 18:
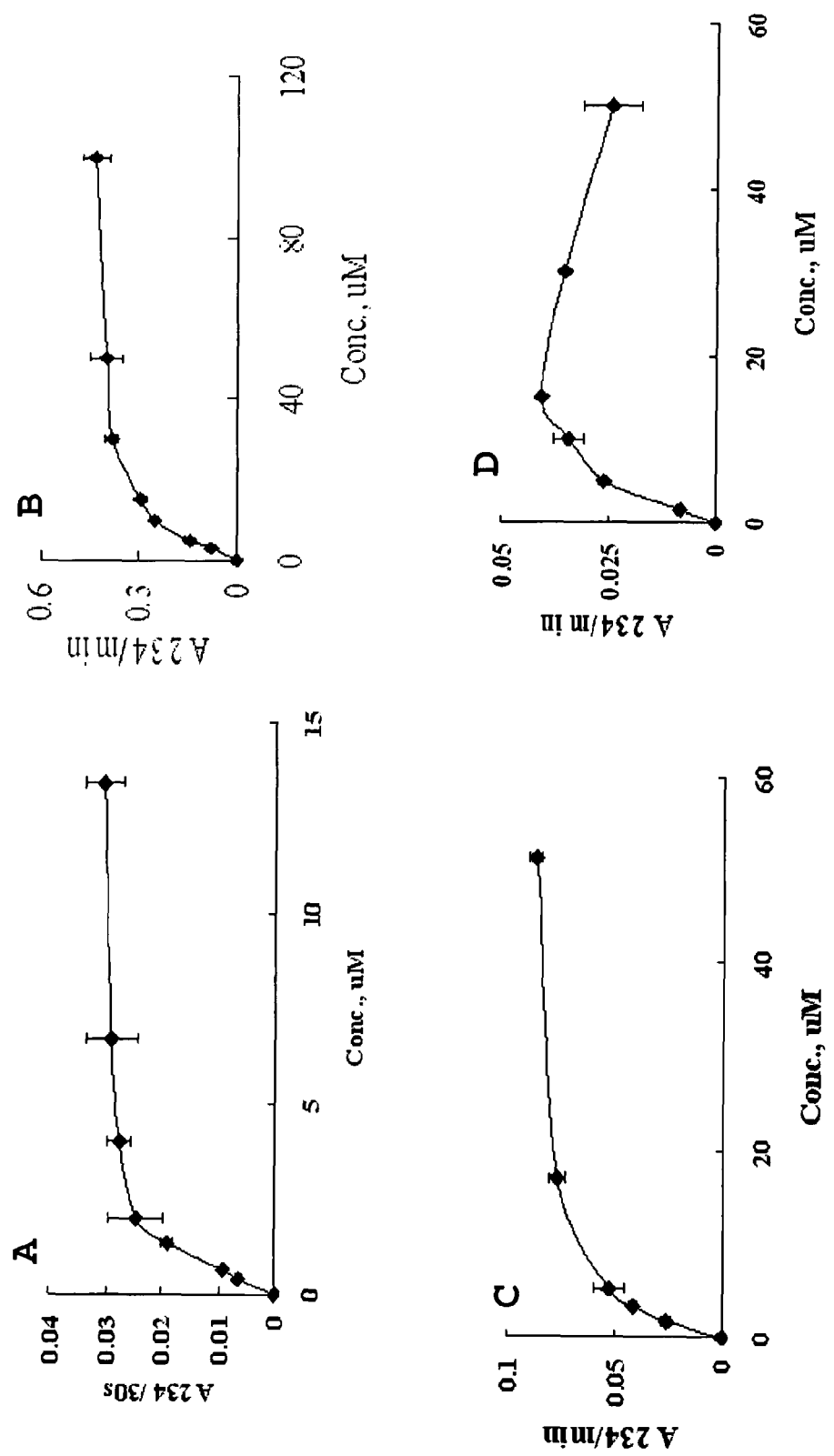
FIGS. 18A-D are diagrams showing the effect by substrate concentration on LOX-catalyzed oxygenation of docosahexaenoyl-lysoPC or docosahexaenoyl-lysoPA.

Determination of Kinetic Values in LOX-Catalyzed Oxygenation of 1-docosahexenoylated Lipids Subsequently, the effect of substrate concentration on LOX-catalyzed oxygenation of 1-docosahexenoyl-lysoPC or 1-docosahexenoyl-lysoPA was examined. Soybean LOX-1 (2.5 units/ml) was incubated with 1-docosahexenoyl-lysoPC (A) or 1-docosahexenoyl-lysoPA (B) of various concentrations (3-60 µM) in borax buffer (50 mM, pH 9.0). Separately, leukocyte LOX (1 unit/ml) was incubated with 1-docosahexenoyl-lysoPC (C) or 1-docosahexenoyl-lysoPA (D) of various concentrations (3-100 µM) in 100 mM phosphate buffer (pH 7.5) containing 5 mM EDTA and 0.03% Tween 20. As demonstrated in FIG. 18, the enzyme activity followed classical Michaelis-Menten kinetics when each enzyme was incubated with 1-docosahexenoyl-lysoPC or 1-docosahexenoyl-lysoPA at various concentrations. Overall, 1-docosahexenoyl-lysoPC (FIGS. 18A & 18C) reached a maximal oxygenation rate at smaller concentrations than 1-docosahexenoyl-lysoPA (FIGS. 18B & 18D).

EXAMPLE 5

Absorbance Measurement of pH-Dependent Oxygenation

Figure 7:
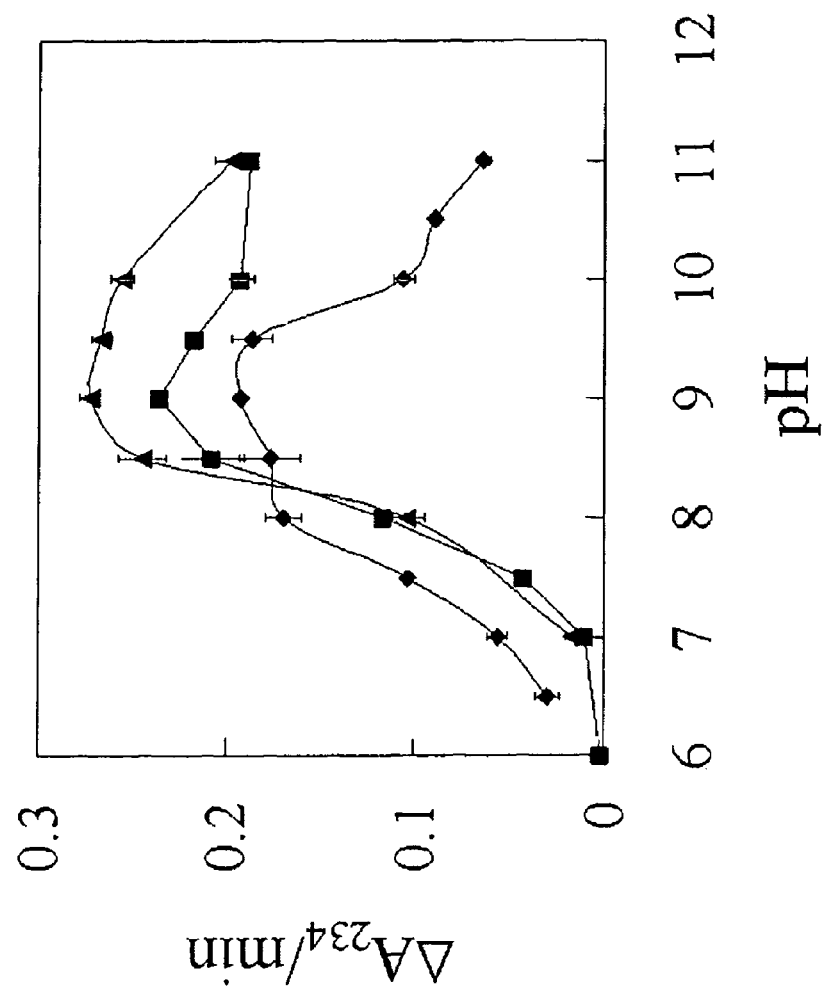
FIG. 7 is an absorbance-pH graph showing the effect of pH on the rate of LOX-1-catalyzed oxygenation of linoleoyl-lysoPC where LOX-1 (0.02 units/ml) was incubated with 100 µM of linoleoyl-lysoPC (■), 100 µM of sodium linoleate (●) or 250 µM of soybean LPC (▲) in buffers of various pHs; 200 mM phosphate (pH 6-8), 50 mM borax (pH 8.5-9.5) and 300 mM sodium bicarbonate (pH 10-11).

LO (840 units/ml Sigma, Saint Louis, Mo., USA) was incubated with 1-linoleoyl-lysophosphatidylcholine (100 µM) in 0.5 ml of buffers of various pHs (pH 6.0-11) as shown in Table 4 for 30 sec at 25° C. FIG. 7 shows the change in initial velocity of absorbance at 234 nm. In addition, FIG. 7 shows the change of absorbance by the same method using soybean lysophosphatidylcholine including 42% of 1-linoleoyl lysophosphatidylcholine (Avanti Polar Lipid Inc, Alasbaster, Ala., USA), linoleic acid (Sigma, Saint Louis, Mo., USA) as substrate of LOX. Linoleic acid was used as substrate together with Tween 20 (0.025 mM).

TABLE 4

LOX activity on various pH conditions

| pH | 1-linoleoyl lysophosphatidylcholine | Soybean lysophosphatidylcholine | linoleic acid |
|---|---|---|---|
| 6 | O | O | X |
| 6.5 | X | X | O |
| 7 | O | O | O |
| 7.5 | O | X | O |
| 8 | O | O | O |
| 8.5 | O | O | O |
| 9 | O | O | O |
| 9.5 | X | O | O |
| 10 | O | O | O |
| 10.5 | X | X | O |
| 11 | O | O | O |

EXAMPLE 6

Comparison of Lipoxygenase Activity on Various Substrates

Reticulocyte LOX (8.2 units/ml) was incubated with each substrate, linoleic acid, linoleoyl-lysoPC or linoleoyl-lysoPA, of various concentrations (3-100 µM) in 500 µl of 50 mM phosphate buffer (pH 7.4) at 25° C. Kinetic values obtained from Lineweaver Burk plot as described before were shown in Table 5. Data were expressed as means ±S.D. of results from at least three independent experiments.

TABLE 5

Kinetic parameters in oxygenation of inoleoylated substrates by reticulocyte LOX

| | Km (µM) | Vm (units/mg) | Vm/Km (units/mg/µM) |
|---|---|---|---|
| Linoleic acid | 12.1 ± 0.80 | 545 ± 5 | 45 ± 2 |
| Linoleoyl-lysoPC | 17.5 ± 0.90 | 1622 ± 19 | 93 ± 4 |
| Linoleoyl-lysoPA | 8.3 ± 0.60 | 443 ± 9 | 54 ± 3 |
| Dilinoleoyl-PC | 71.7 ± 6.90 | 646 ± 20 | 9 ± 1 |
| Dilinoleoyl-PA | 90.0 ± 7.30 | 1029 ± 22 | 11 ± 1 |

Porcine leukocyte LOX (1.5 units/ml) was incubated with each substrate (linoleic acid, linoleoyl-lysoPC or linoleoyl-lysoPA) of various concentrations (3-100 µM) in 500 µl of 100 mM phosphate buffer (pH 7.5) containing 5 mM EDTA and 0.03% Tween 20 at 25° C. Kinetic values obtained from Lineweaver Burk plot as described before were shown in Table 6. Data were expressed as means ±S.D. of results from at least three independent experiments.

TABLE 6

Kinetic parameters in oxygenation of linoleoylated substrates by leukocyte LOX

| | Km (µM) | Vm (units/mg) | Vm/Km (units/mg/µM) |
|---|---|---|---|
| Linoleic acid | 31.2 ± 4.6 | 32.7 ± 1.93 | 1.07 ± 0.19 |
| Linoleoyl-lysoPC | 15.1 ± 1.34 | 14.42 ± 0.78 | 0.96 ± 0.13 |
| Linoleoyl-lysoPA | 35.5 ± 3.77 | 30.7 ± 0.78 | 0.87 ± 0.079 |

Tables 5 and 6 demonstrate that linoleoyl-lysoPC and linoleoyl-lysoPA may be efficient substrates for reticulocyte LOX as well as leukocyte LOX, since they are as efficient as linoleic acid as substrates. Noteworthy, linoleoyl-lysoPC is more efficient than linoleic acid as a substrate for reticulocyte LOX. The greater efficacy of linoleoyl-lysoPC as a substrate for reticulocyte LOX, compared to soybean LOX-1 (Huang et al, Arch. Biochem. Biophys. 455 (2006) 119-126), suggests that linoleoyl-lysoPC may be a favorable substrate for reticulocyte lipoxygenase.

Soybean LOX-1 (2.5 units/ml) was incubated with docosahexaenoyl-lysoPC, didocosahexaenoyl-lysoPC or docosahexaenoic acid of various concentrations in 500 µl of 50 mM borax buffer (pH 9.0) at 25° C. Kinetic values obtained from Lineweaver Burke plot as described before were shown in Table 7. Values were expressed as means ±S.D. of results from at least three independent experiments.

TABLE 7

Kinetic values in oxygenation of docosahexaenoic acid derivatives by soybean LOX-1.

| | Km (µM) | Vm (units/µg) | Vm/Km (units/µg/µM) |
|---|---|---|---|
| Docosahexaenoic acid | 16.8 ± 1.4 | 178.0 ± 7.4 | 10.3 ± 1.3 |
| Docosahexaenoyl-lysoPC | 2.2 ± 0.6 | 104.2 ± 5.2 | 42.4 ± 7.2 |
| Didocosahexaenoyl-PC | 1072 ± 184 | 7.8 ± 0.3 | 0.007 ± 0.001 |

Porcine leukocyte LOX (2 units/ml) was incubated with each substrate docosahexaenoyl-lysoPC or docosahexaenoic acid of various concentrations in 500 µl of 100 mM phosphate buffer (pH 7.4) containing 5 mM EDTA and 0.03% Tween 20 at 25° C. Kinetic values obtained from Lineweaver Burke plot were shown in Table 8.

TABLE 8

| | Km (μM) | Vm (units/mg) | Vm/Km (units/mg/μM) |
|---|---|---|---|
| Docosahexaenoic acid | 17.6 ± 1.7 | 35.9 ± 0.5 | 2.1 ± 0.9 |
| Docosahexaenoyl-lysoPC | 3.4 ± 1.8 | 77.2 ± 2.8 | 22.7 ± 0.8 |

Kinetic values in oxygenation of docosahexaenoyl-lysoPC or docosahexaenoic acid by leukocyte LOX.

Tables 7 and 8 demonstrate that docosahexaenoyl-lysoPC is also oxygenated efficiently by soybean LOX-1 and leukocyte LOX, implying that docosahexaenoyl-lysoPC may be utilized as an efficient substrate. Moreover, the greater efficacy of docosahexaenoyl-lysoPC, as compared to docosahexaenoic acid, as a substrate for soybean LOX-1 suggests that docosahexaenoyl-lysoPC, relatively polar, may be a favorable substrate for soybean LOX-1.

As described above, the methods according to the invention can simply and precisely analyze lipoxygenase activity. Thus the present invention can be used to various kinds of studies on lipoxygenases, such as 12-lipoxygenase or 15-lipoxygeanse, related to diseases such as inflammation, immunology, allergy, asthma etc.

Although the present invention has been described with reference to several exemplary embodiments, the description is illustrative of the invention and is not to be construed as limiting the invention. Various modifications, variations and replacements may occur to those skilled in the art, without departing from the spirit and scope of the invention as defined by the appended claims.

What is claimed is:

1. A method for analyzing the activity of lipoxygenase, comprising the steps of:
    (a) adding polyunsaturated lysophosphatidylcholine as a water-soluble substrate into a reaction solution;
    (b) adding lipoxygenase into the reaction solution; and
    (c) measuring spectral characteristics of the reaction solution to obtain spectral data, wherein said polyunsaturated lysophosphatidylcholine is selected from the group consisting of 1-linoleoyl lysophosphatidylcholine, 1-arachidonoyl lysophosphatidylcholine and docosahexaenoyl lysophosphatidylcholine.

2. The method according to claim 1, wherein said lipoxygenase originates from a plant or an animal.

3. The method according to claim 1, wherein said lipoxygenase originates from a plant cell or an animal cell.

4. The method according to claim 1, wherein said 1-linoleonyl lysophosphatidylcholine, 1 arachidonoyl lysophosphatidylcholine and docosahexaenoyl lysophosphatidylcholine comprise one or more radioisotope of $^{14}C$ or $^{32}P$.

5. The method according to claim 1, wherein the lipoxygenase activity is measured by using absorbance at 234 nm.

6. The method according to claim 1, wherein the lipoxygenase activity is measured by measuring peroxide of the water-soluble substrate.

7. The method according to claim 6, wherein said peroxide is 1-(13-hydroperoxy)linoleoyl lysophosphatidylcholine in case the substrate is 1-linoleoyl lysophosphatidylcholine; 1-(15-hydroperoxy) arachidonoyl lysophosphatidylcholine in case the substrate is arachidonoyl lysophosphatidylcholine; and 1-(17-hydroperoxy)docosahexaenoyl lysophosphatidylcholine in case the substrate is docosahexaenoyl lysophosphatidylcholine.

8. The method according to claim 1, wherein the lipoxygenase is measured in the reaction solution in range of pH 5-11.

9. The method according to claim 1, wherein the concentration of the substrate is in the range of 0.0001-1 mM in the reaction solution.

* * * * *

UNITED STATES PATENT AND TRADEMARK OFFICE
CERTIFICATE OF CORRECTION

| | | |
|---|---|---|
| PATENT NO. | : 7,939,290 B2 | |
| APPLICATION NO. | : 11/801482 | |
| DATED | : May 10, 2011 | |
| INVENTOR(S) | : Kim et al. | |

It is certified that error appears in the above-identified patent and that said Letters Patent is hereby corrected as shown below:

Title page, item [30] Priority add

--Korean Application No. 10-2006-0041501 filed May 9, 2006--

Signed and Sealed this
Twelfth Day of July, 2011

David J. Kappos
*Director of the United States Patent and Trademark Office*